United States Patent
Kieval et al.

(10) Patent No.: US 7,616,997 B2
(45) Date of Patent: Nov. 10, 2009

(54) DEVICES AND METHODS FOR CARDIOVASCULAR REFLEX CONTROL VIA COUPLED ELECTRODES

(76) Inventors: Robert S. Kieval, 850 Foxberry Cir., Medina, MN (US) 55340; Bruce J. Persson, 6389 64th La., Albertville, MN (US) 55301; David J. Serdar, 6030 Chestnut Ct., Shorewood, MN (US) 55331; Peter T. Keith, 1477 Grantham St., St. Paul, MN (US) 55108; Martin A. Rossing, 1930 127th Cir. NW., Coon Rapids, MN (US) 55448

( * ) Notice: Subject to any disclaimer, the term of this patent is extended or adjusted under 35 U.S.C. 154(b) by 403 days.

(21) Appl. No.: 10/402,393

(22) Filed: Mar. 27, 2003

(65) Prior Publication Data

US 2004/0019364 A1 Jan. 29, 2004

Related U.S. Application Data

(63) Continuation-in-part of application No. 09/964,079, filed on Sep. 26, 2001, now Pat. No. 6,985,774, which is a continuation-in-part of application No. 09/671,850, filed on Sep. 27, 2000, now Pat. No. 6,522,926.

(60) Provisional application No. 60/368,222, filed on Mar. 27, 2002.

(51) Int. Cl.
*A61N 1/18* (2006.01)
(52) U.S. Cl. .......................................... 607/44; 607/60
(58) Field of Classification Search ................. 600/377, 600/381, 505; 607/44, 60, 62, 116, 118
See application file for complete search history.

(56) References Cited

U.S. PATENT DOCUMENTS 3,522,811 A 8/1970 Schwartz et al.

(Continued)

FOREIGN PATENT DOCUMENTS

| WO | WO 97/18856 | * | 5/1997 |
| WO | WO 98/02209 | | 1/1998 |
| WO | WO 99/26530 | | 6/1999 |
| WO | WO 99/42039 | | 8/1999 |

(Continued)

OTHER PUBLICATIONS

Cardiovascular Reflexes From Ventricular & Coronary Receptors, *Adv. Exp. Med. Biol.*, 1995, 381:157-74.

(Continued)

*Primary Examiner*—Mark W Bockelman
*Assistant Examiner*—Eric D Bertram
(74) *Attorney, Agent, or Firm*—Patterson, Thuente, Skaar & Christensen, P.A.

(57) ABSTRACT

Devices, systems and methods are disclosed by which the blood pressure, nervous system activity, and neurohormonal activity may be selectively and controllably reduced by activating baroreceptors. A baroreceptor activation device is positioned near a baroreceptor, preferably a baroreceptor located in the carotid sinus. A control system may be used to modulate the baroreceptor activation device. The control system may utilize an algorithm defining a stimulus regimen which promotes long term efficacy and reduces power requirements/consumption. The baroreceptor activation device may utilize RF-coupled or other electrodes to activate the baroreceptors. The electrodes may be adapted for connection to the carotid arteries at or near the carotid sinus, and may be designed to minimize extraneous tissue stimulation.

3 Claims, 19 Drawing Sheets

U.S. PATENT DOCUMENTS

| | | | |
|---|---|---|---|
| 3,645,267 | A | 2/1972 | Hagfors |
| 3,650,277 | A | 3/1972 | Sjostrand et al. |
| 3,943,936 | A | 3/1976 | Rasor et al. |
| 4,014,318 | A | 3/1977 | Dockum et al. |
| RE30,366 | E | 8/1980 | Rasor et al. |
| 4,256,094 | A | 3/1981 | Kapp et al. |
| 4,323,073 | A | 4/1982 | Ferris |
| 4,331,157 | A | 5/1982 | Keller, Jr. et al. |
| 4,481,953 | A | 11/1984 | Gold et al. |
| 4,525,074 | A | 6/1985 | Murakami |
| 4,531,943 | A | 7/1985 | Van Tassel et al. |
| 4,551,862 | A | 11/1985 | Habor |
| 4,573,481 | A | 3/1986 | Bullara |
| 4,586,501 | A | 5/1986 | Claracq |
| 4,590,946 | A | 5/1986 | Loeb et al. |
| 4,640,286 | A | 2/1987 | Thomson |
| 4,641,664 | A | 2/1987 | Botvidsson |
| 4,664,120 | A | 5/1987 | Hess |
| 4,682,583 | A | 7/1987 | Burton et al. |
| 4,702,254 | A | 10/1987 | Zabara |
| 4,709,690 | A | 12/1987 | Habor |
| 4,719,921 | A | 1/1988 | Chirife |
| 4,739,762 | A | 4/1988 | Palmaz |
| 4,762,130 | A | 8/1988 | Fogarty et al. |
| 4,762,820 | A | 8/1988 | Gavras |
| 4,770,177 | A | 9/1988 | Schroeppel |
| 4,791,931 | A | 12/1988 | Slate |
| 4,800,882 | A | 1/1989 | Gianturco |
| 4,803,988 | A | 2/1989 | Thomson |
| 4,813,418 | A | 3/1989 | Harris |
| 4,825,871 | A | 5/1989 | Cansell |
| 4,828,544 | A | 5/1989 | Lane et al. |
| 4,830,003 | A | 5/1989 | Wolff et al. |
| 4,860,751 | A | 8/1989 | Callaghan |
| 4,867,164 | A | 9/1989 | Zabara |
| 4,881,939 | A | 11/1989 | Newman |
| 4,886,062 | A | 12/1989 | Wiktor |
| 4,887,608 | A | 12/1989 | Mohl et al. |
| 4,917,092 | A | 4/1990 | Todd et al. |
| 4,960,133 | A | 10/1990 | Hewson |
| 4,967,159 | A * | 10/1990 | Manes ........................ 324/650 |
| 4,969,458 | A | 11/1990 | Wiktor |
| 4,987,897 | A | 1/1991 | Funke |
| 5,025,807 | A | 6/1991 | Zabara |
| 5,040,533 | A | 8/1991 | Fearnot |
| 5,078,736 | A | 1/1992 | Behl |
| 5,113,859 | A | 5/1992 | Funke |
| 5,113,869 | A | 5/1992 | Nappholz et al. |
| 5,117,826 | A | 6/1992 | Bartelt et al. |
| 5,170,802 | A | 12/1992 | Mehra |
| 5,181,911 | A | 1/1993 | Shturman |
| 5,199,428 | A * | 4/1993 | Obel et al. .................... 607/44 |
| 5,215,089 | A | 6/1993 | Baker, Jr. |
| 5,222,971 | A | 6/1993 | Willard et al. |
| 5,224,491 | A | 7/1993 | Mehra |
| 5,259,394 | A | 11/1993 | Bens |
| 5,282,468 | A | 2/1994 | Klepinski |
| 5,295,959 | A | 3/1994 | Gurbel et al. |
| 5,299,569 | A | 4/1994 | Wernicke et al. |
| 5,304,206 | A | 4/1994 | Baker, Jr. et al. |
| 5,314,453 | A | 5/1994 | Jeutter |
| 5,318,592 | A | 6/1994 | Schaldach |
| 5,330,507 | A | 7/1994 | Schwartz |
| 5,330,515 | A | 7/1994 | Rutecki et al. |
| 5,331,966 | A | 7/1994 | Bennett et al. |
| 5,351,394 | A | 10/1994 | Weinberg |
| 5,411,535 | A * | 5/1995 | Fujii et al. .................... 607/32 |
| 5,411,540 | A | 5/1995 | Edell et al. |
| 5,458,626 | A | 10/1995 | Krause |
| 5,509,888 | A | 4/1996 | Miller |
| 5,522,854 | A | 6/1996 | Ideker et al. |
| 5,529,067 | A | 6/1996 | Larsen et al. |
| 5,531,766 | A | 7/1996 | Kroll et al. |
| 5,531,779 | A | 7/1996 | Dahl et al. |
| 5,535,752 | A | 7/1996 | Halperin et al. |
| 5,540,734 | A | 7/1996 | Zabara |
| 5,540,735 | A | 7/1996 | Wingrove |
| 5,545,132 | A | 8/1996 | Fagan et al. |
| 5,545,202 | A | 8/1996 | Dahl et al. |
| 5,571,150 | A | 11/1996 | Wernicke et al. |
| 5,575,809 | A | 11/1996 | Sasaki |
| 5,578,061 | A | 11/1996 | Stroetmann et al. |
| 5,634,878 | A | 6/1997 | Grundei et al. |
| 5,643,330 | A | 7/1997 | Holsheimer et al. |
| 5,651,378 | A | 7/1997 | Matheny et al. |
| 5,683,430 | A * | 11/1997 | Markowitz et al. ............ 607/27 |
| 5,690,681 | A | 11/1997 | Geddes et al. |
| 5,692,882 | A | 12/1997 | Bozeman, Jr. et al. |
| 5,695,468 | A | 12/1997 | Lafontaine et al. |
| 5,700,282 | A | 12/1997 | Zabara |
| 5,707,400 | A | 1/1998 | Terry, Jr. et al. |
| 5,715,837 | A | 2/1998 | Chen |
| 5,725,471 | A | 3/1998 | Davey et al. |
| 5,725,563 | A | 3/1998 | Klotz |
| 5,727,558 | A * | 3/1998 | Hakki et al. ................. 600/485 |
| 5,741,316 | A | 4/1998 | Chen et al. |
| 5,766,236 | A | 6/1998 | Detty et al. |
| 5,800,464 | A | 9/1998 | Kieval |
| 5,807,258 | A | 9/1998 | Cimochowski et al. |
| 5,810,735 | A | 9/1998 | Halperin et al. |
| 5,814,079 | A | 9/1998 | Kieval |
| 5,824,021 | A | 10/1998 | Rise |
| 5,861,015 | A | 1/1999 | Benja-Athon |
| 5,876,422 | A | 3/1999 | van Groeningen |
| 5,891,181 | A | 4/1999 | Zhu |
| 5,904,708 | A | 5/1999 | Goedeke |
| 5,913,876 | A | 6/1999 | Taylor et al. |
| 5,916,239 | A | 6/1999 | Geddes et al. |
| 5,919,220 | A | 7/1999 | Stieglitz et al. |
| 5,928,272 | A | 7/1999 | Adkins et al. |
| 5,938,596 | A | 8/1999 | Woloszko et al. |
| 5,954,761 | A | 9/1999 | Machek et al. |
| 5,967,986 | A | 10/1999 | Cimochowski et al. |
| 5,967,989 | A | 10/1999 | Cimochowski et al. |
| 5,987,352 | A | 11/1999 | Klein et al. |
| 5,989,230 | A | 11/1999 | Frassica |
| 6,006,134 | A | 12/1999 | Hill et al. |
| 6,016,449 | A | 1/2000 | Fischell et al. |
| 6,023,642 | A | 2/2000 | Shealy et al. |
| 6,050,952 | A | 4/2000 | Hakki et al. |
| 6,052,623 | A | 4/2000 | Fenner et al. |
| 6,058,331 | A | 5/2000 | King |
| 6,061,596 | A | 5/2000 | Richmond et al. |
| 6,073,048 | A | 6/2000 | Kieval et al. |
| 6,077,227 | A | 6/2000 | Miesel et al. |
| 6,077,298 | A | 6/2000 | Tu et al. |
| 6,106,477 | A | 8/2000 | Miesel et al. |
| 6,141,588 | A * | 10/2000 | Cox et al. ....................... 607/9 |
| 6,161,029 | A | 12/2000 | Spreigl et al. |
| 6,178,349 | B1 | 1/2001 | Kieval |
| 6,178,379 | B1 | 1/2001 | Kieval |
| 6,206,914 | B1 * | 3/2001 | Soykan et al. ............... 623/1.42 |
| 6,208,894 | B1 | 3/2001 | Schulman et al. |
| 6,231,516 | B1 | 5/2001 | Keilman et al. |
| 6,292,695 | B1 | 9/2001 | Webster, Jr. et al. |
| 6,292,703 | B1 | 9/2001 | Meier et al. |
| 6,397,109 | B1 * | 5/2002 | Cammilli et al. ............ 607/123 |
| 6,438,428 | B1 | 8/2002 | Axelgaard et al. |
| 6,442,413 | B1 | 8/2002 | Silver et al. |
| 6,445,953 | B1 | 9/2002 | Bulkes et al. |
| 6,522,926 | B1 | 2/2003 | Kieval et al. |
| 6,564,101 | B1 | 5/2003 | Zikria |
| 6,907,285 | B2 | 6/2005 | Denker et al. |
| 6,985,774 | B2 | 1/2006 | Kieval et al. |

| | | | |
|---|---|---|---|
| 7,155,284 | B1 | 12/2006 | Whitehurst et al. |
| 7,158,832 | B2 | 1/2007 | Kieval et al. |
| 7,236,821 | B2 | 6/2007 | Cates et al. |
| 2001/0020177 | A1 | 9/2001 | Gruzdowich et al. |
| 2002/0005982 | A1 | 1/2002 | Borlinghaus |
| 2002/0026228 | A1 | 2/2002 | Schauerte |
| 2002/0103516 | A1 | 8/2002 | Patwardhan et al. |
| 2002/0151051 | A1 | 10/2002 | Li |
| 2003/0040785 | A1 | 2/2003 | Maschino et al. |
| 2004/0010303 | A1 | 1/2004 | Bolea et al. |
| 2008/0167699 | A1 | 7/2008 | Kieval et al. |

FOREIGN PATENT DOCUMENTS

| | | |
|---|---|---|
| WO | WO 99/42176 | 8/1999 |
| WO | WO 00/16686 | 3/2000 |
| WO | WO 01/00273 A | 1/2001 |

OTHER PUBLICATIONS

"Non-Invasive Heat-Delivery To Arterial Stented Segments In Vivo: Effect of Heat on Intimal Hyperplasia", *JACC*, 1041-89, Feb. 2000.
"The Haemodynamic Basis of Anginal Relief Produced By Stimulation of the Carotid Sinus Nerve", *Acta Medica Academiae Scientiarum Hungaricae*, 30 (1-2), pp. 61-65, 1973.
Correspondence, *The New England of Journal of Medicine*, vol. 281, Jul. 3, 1969, No. 2.
"Carotid Sinus Stimulation For the Treatment of Angina Pectoris", *Official Journal of the Calif. Medical Assoc.*, vol. 12, No. 3, pp. 78-79, Mar. 1970.
"Circulatory Effects of Carotid Sinus Stimulation & Changes in Blood Volume Distribution in Hypertensive Man", *Acta. Physiol. Scand.*, 1981, 111:299-306, Mar. 1981.
"Surgical Treatment of Hypertension with Reference to Baropacing", *The Amer. Jour. Of Cardiology*, vol. 17, May 1966, pp. 663-667.
"Baropacing of the Carotid Sinus Nerve for Treatment of Intractable Hypertension", Zeitschrift Fur Kardiologie, band 64, Heft 4, pp. 368-374, 1975.
"Laryngospasm Induced by a Carotid-Sinus-Nerve Stimulator", The New England *Journ. Of Med.*, No. 13, pp. 709-710, undated.
"Fine Structure of Baroreceptor Terminals in the Carotid Sinus of Guinea Pigs & Mice", *Cell & Tissue Research*, 170, pp. 95-112, 1976.
"Structure of Rat Aortic Baroreceptors & Their Relationship to Connective Tissue", *Journal of Neurocytology*, pp. 401-414, 1979.
"Baroreflex Anatomy", *Human Baroreflexes in Health & Disease*, pp. 19-30, 1992.
"Implantation of a Carotid Sinus Nerve Stimulator", *AORN Journal*, pp. 53-56, Dec. 1969.
"The Treatment of Heart Disease", *Heart Disease*, Earl N. Silber, 2.sup.nd Edition, MacMillan Publishing Co., p. 1642, 1987.
"Stimulation of the Carotid Baroreceptors Using a Radio-Frequency Method", Israel *J. Med. Sci.*, vol. 1, No. 4, Jul. 1965, pp. 630-632.
"Studies on the Carotid Body & the Carotid Sinus Effects on the Heart by Electrical Stimulation of the Carotid Sinus Wall", *Jap. Heart J.*, vol. 13, No. 2, Mar. 1972, pp. 136-149.
"Abstracts of the 40.sup.th Scientific Sessions", Supplement II to Circulation, vols. XXXV & XXXVI, Oct. 1967, II-253, 1 sheet.

"Clinical Experience with a Helical Bipolar Stimulating Lead", PACE, vol. 15, Part II, Oct. 1992, pp. 1545-1556.
Schauerte et al., "Transvenous Parasympathetic Nerve Stimulation in the Inferior Vena Cava and Atrioventricular Conduction", *J Cardiovasc Electrophysiol*, Jan. 2000, 11(1):64-69, 1 page.
Jeffrey J. Goldberger et al., "New Technique for Vagal Nerve Stimulation", *Journal of Neuroscience Methods*, 1999, pp. 109-114.
Bilgutay, A.M. et al., "Baropacing, a New Concept in the Treatment of Hypertension", from Baroreceptors and Hypertension Proceedings of an International Symposium, Nov. 1965, p. 425-437.
Brattstrom, A., Influence of Continuous and Intermittent (R-Wave Triggered) Electrical Stimulation of the Carotid Sinus Nerve on the Static Characteristic of the Circularoty Regulator:, Experientia 28:414-416, 1972.
Peters et al., The Principle of Electrical Carotid Sinus Nerve Stimulation: A Nerve Pacemaker System for Angina Pectoris and Hypertension Therapy, Annals of Biomedical Engineering, 8:445-458, 1980.
Richter et al., The Course of Inhibition of Sympathetic Activity during Various Patterns of Carotid Sinus Nerve Stimulation, Pflugers Arch., 317:110-123, 1970.
Sedin, Gunnar, Responses of the Cardiovascular System to Carotid Sinus Nerve Stimulation, Upsala J Med Sci, 81:1-17, 1976.
Warzel et. al., Effects of carotis sinus nerve stimulation at different times in the respiratory and cardiac cycles on variability of heart rate and blood pressure of normotensive and renal hypertensive dogs, Journal of the Autonomic Nervous System, 26:121-127, 1989.
Warzel et. al., The Effect of Time of Electrical Stimulation of the Carotid Sinus on the Amount of Reduction in Arterial Pressure, Pflugers Arch., 337:39-44, 1972.
Peters et al., "Cardiovascular response to time delays of electrocardiogram-coupled electrical stimulation of carotid sinus nerves in dogs," *Journal of the Autonomic Nervous Systems*, vol. 25, (1988), pp. 173-180.
Peters et al., "Cardiovascular response to time delays of electrocardiogram-coupled electrical stimulation of carotid sinus nerves in dogs," Journal of Autonomic Nervous Systems, 25:173-180, 1988.
Coleridge et al., "Impulse in Slowly Conducting Vagal Fibers from Afferent Endings in the Veins, Atria, and Arteries of Dogs and Cats," *Circ. Res.*, vol. 33, (Jul. 1973), pp. 87-97.
Coleridge et al., "Reflex Effects of Stimulating Baroreceptors in the Pulmonary Artery," *J. Physiol.* (1963) 166:197-210.
Ebert et al., "Fentanyl-Diazepam Anesthesia With or Without N20 Does Not Attenuate Cardiopulmonary Baroreflex-Mediated Vasoconstrictor Responses to Controlled Hypovolemia in Humans," *Anesth. Analg.*
U.S. Appl. No. 09/671,850, Application Data and Image File Wrapper listing.
U.S. Appl. No. 09/964,079, Application Data and Image File Wrapper listing.
U.S. Appl. No. 09/963,991, Application Data and Image File Wrapper listing.
U.S. Appl. No. 11/933,339, Application Data and Image File Wrapper listing.
U.S. Appl. No. 12/421,416, Application Data and Image File Wrapper listing.

* cited by examiner

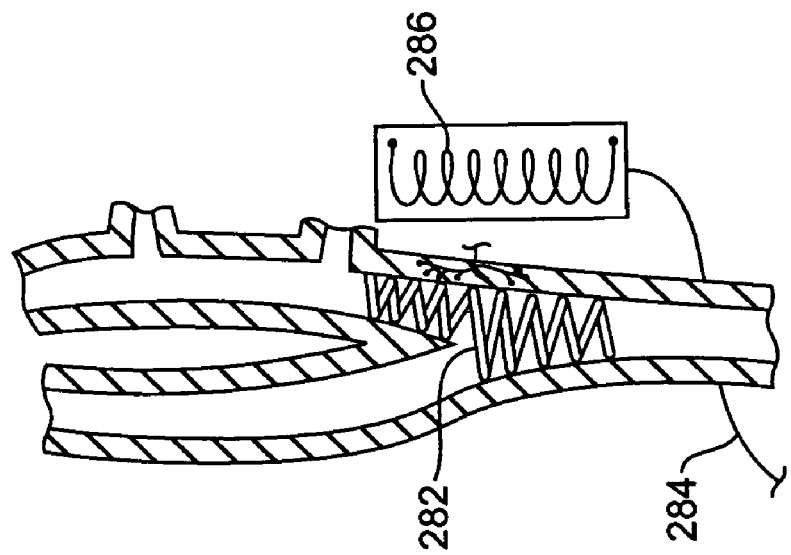
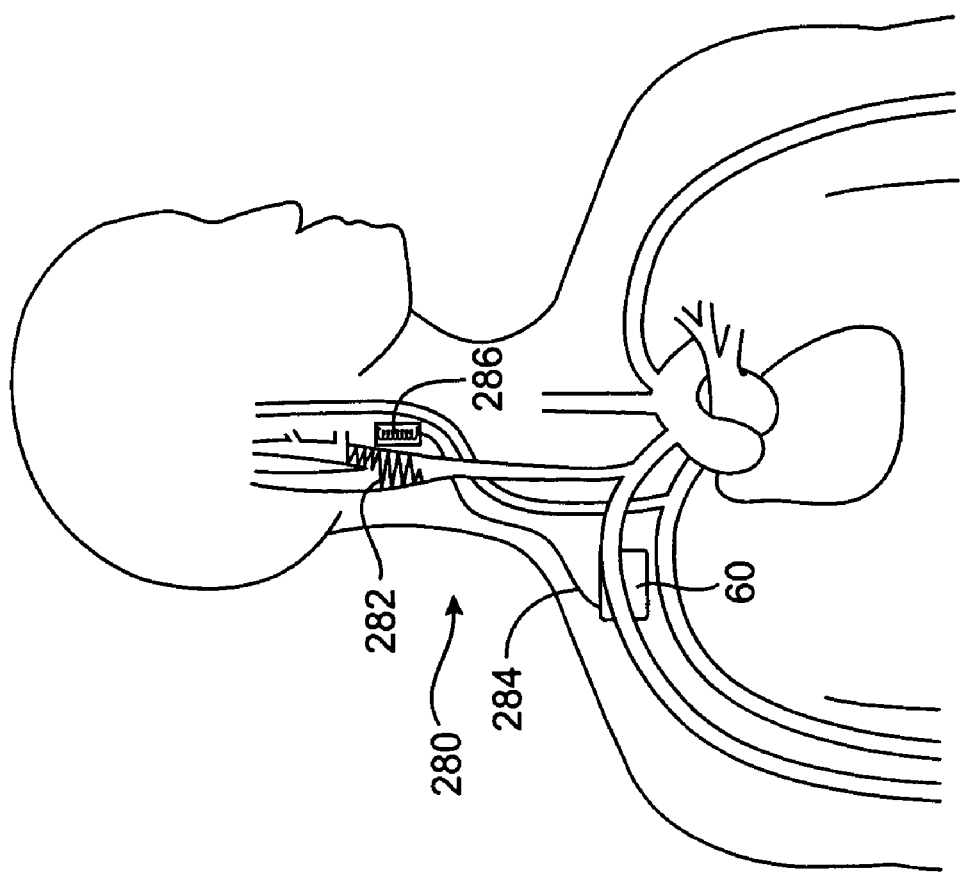
FIG. 5B
FIG. 5A

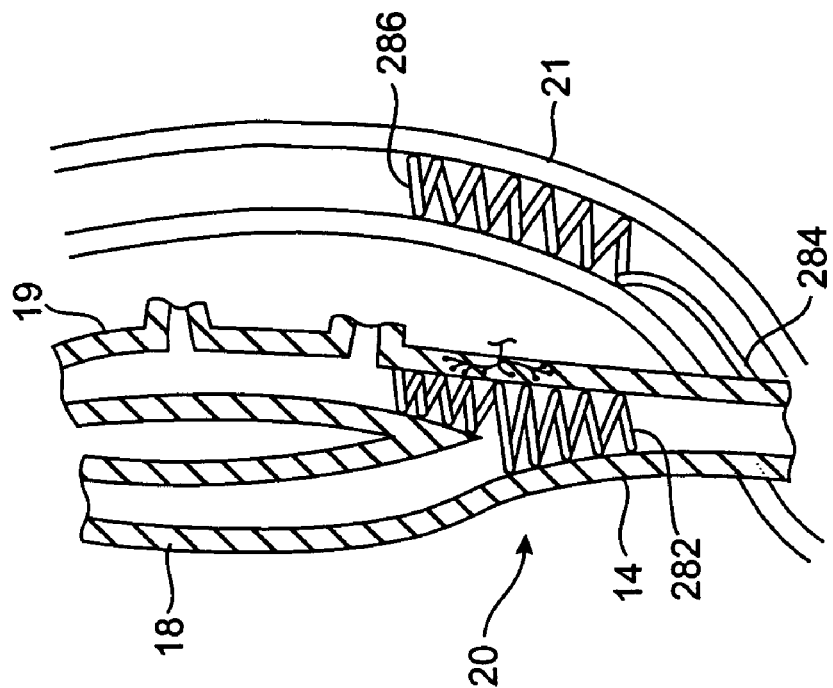
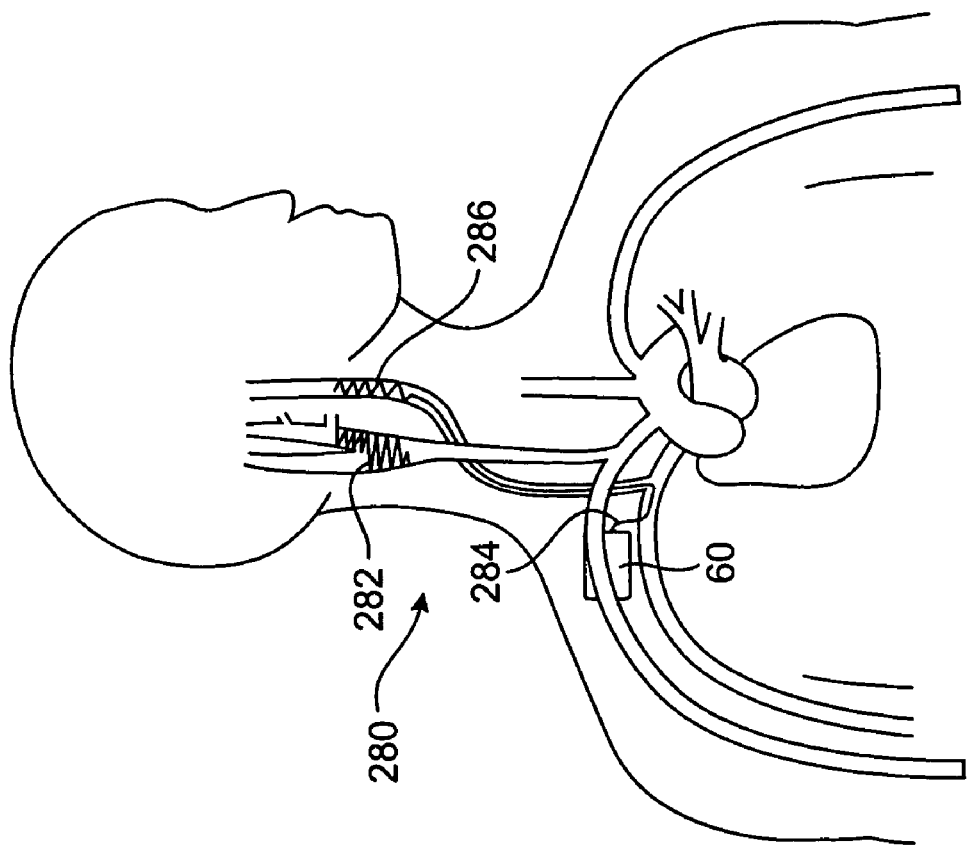

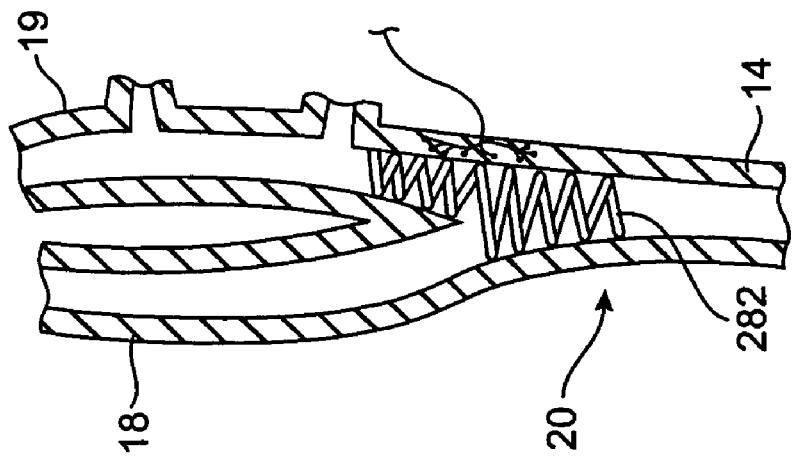
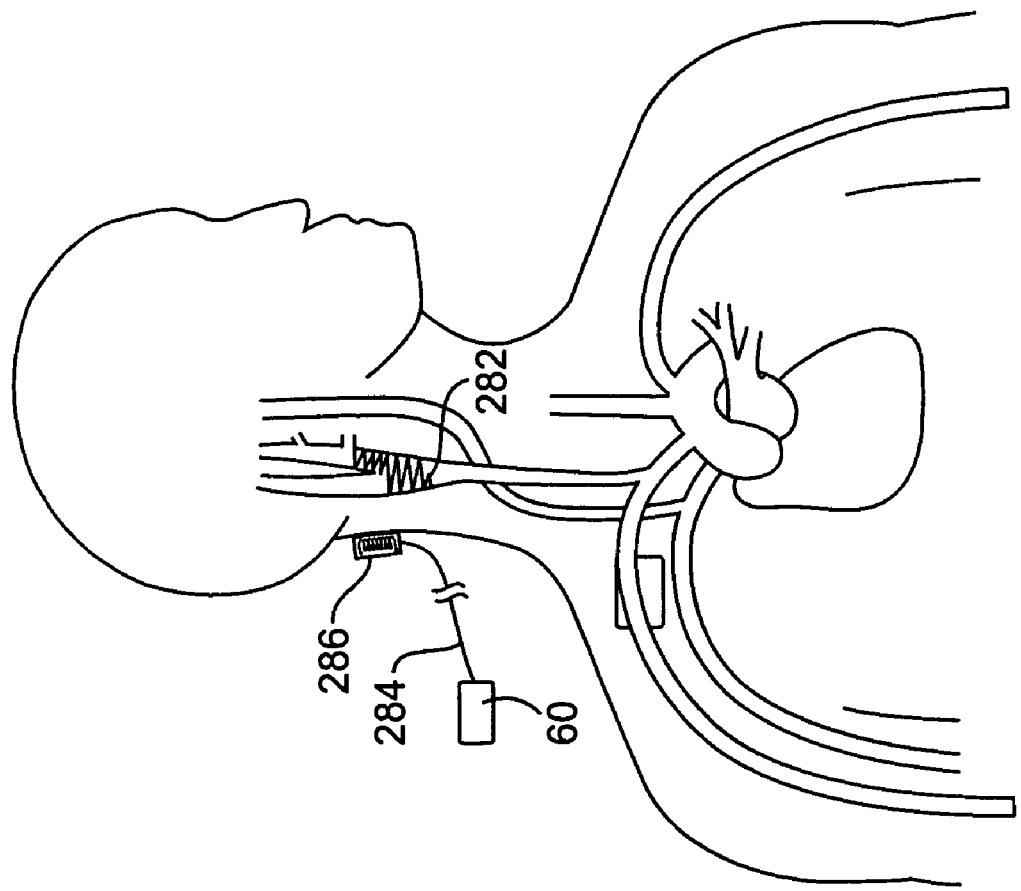
FIG. 7B
FIG. 7A

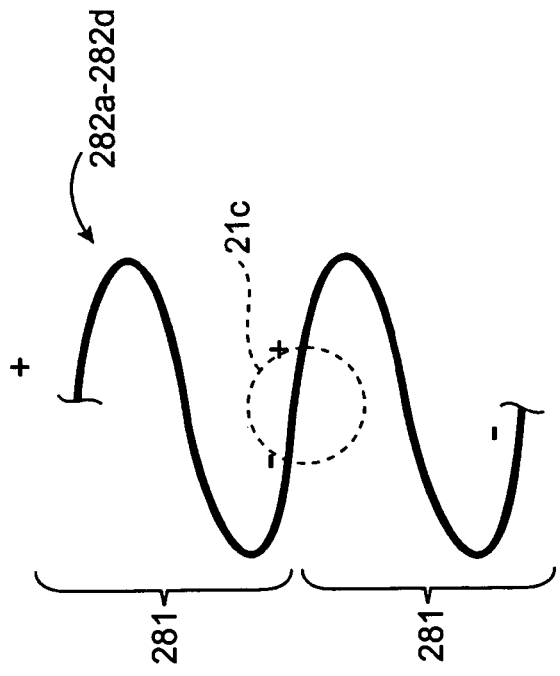
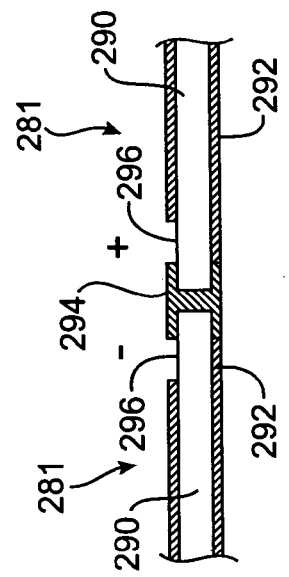
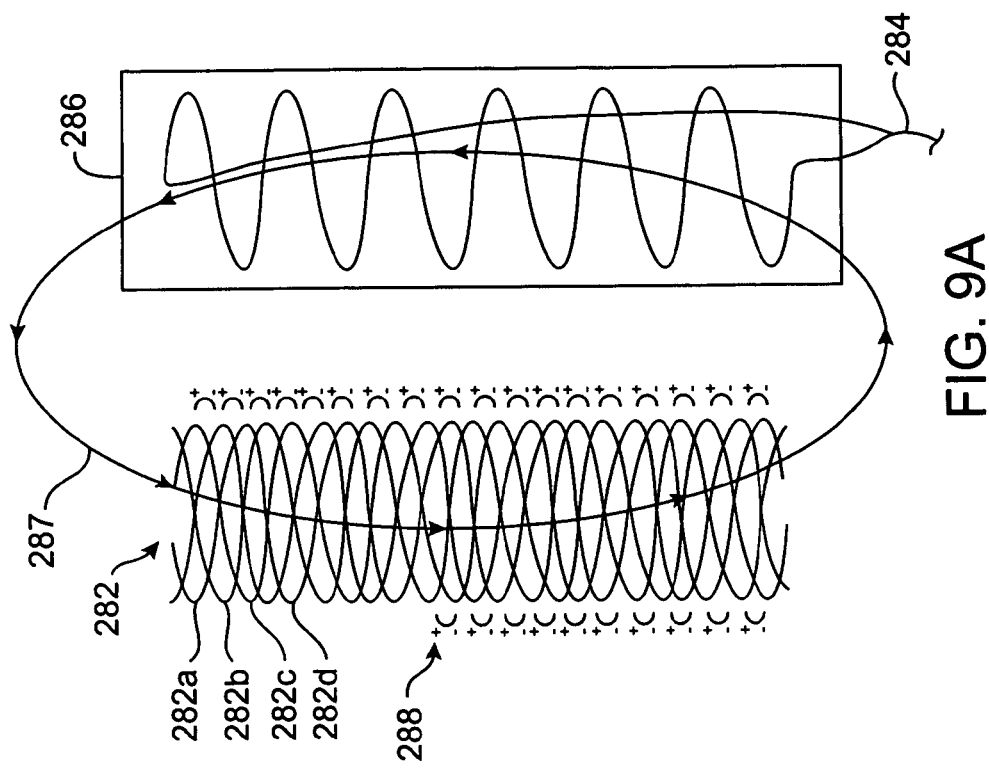
FIG. 9B
FIG. 9C
FIG. 9A

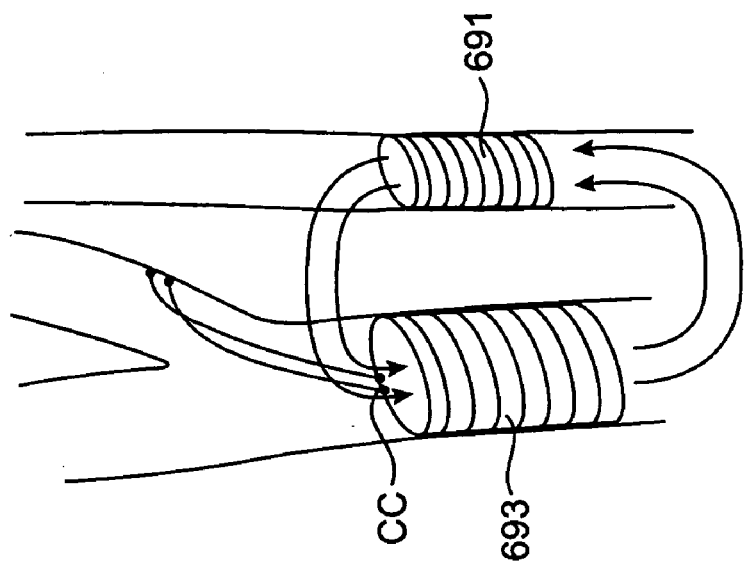
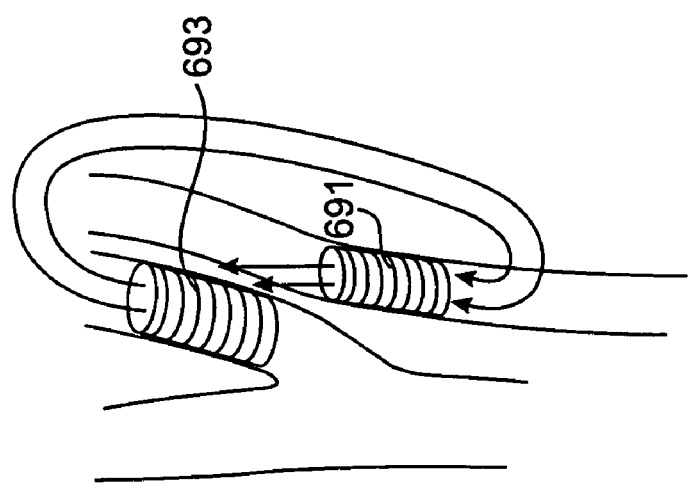
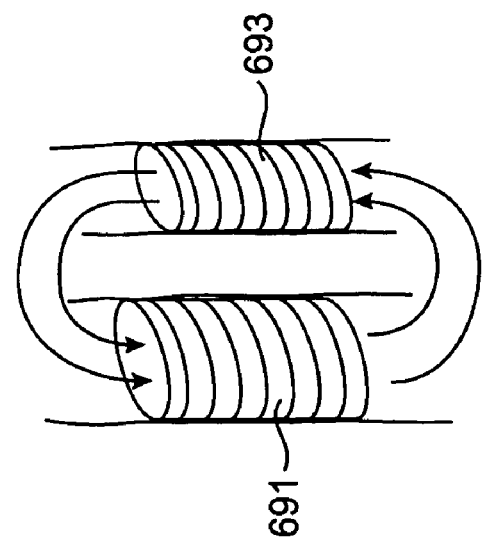

DEVICES AND METHODS FOR CARDIOVASCULAR REFLEX CONTROL VIA COUPLED ELECTRODES

CROSS-REFERENCES TO RELATED APPLICATIONS

This application claims the benefit of provisional application No. 60/368,222, filed on Mar. 27, 2002. This application is also a continuation-in-part of application Ser. No. 09/964,079, filed on Sep. 26, 2001, now U.S. Pat. No. 6,985,774, which was a continuation-in-part of application Ser. No. 09/671,850, filed on Sep. 27, 2000, now U.S. Pat. No. 6,522,926, the full disclosures of which are incorporated herein by reference.

BACKGROUND OF THE INVENTION

1. Field of the Invention

The present invention generally relates to medical devices and methods of use for the treatment and/or management of cardiovascular and renal disorders. Specifically, the present invention relates to devices and methods for controlling the baroreflex system for the treatment and/or management of cardiovascular and renal disorders and their underlying causes and conditions.

Cardiovascular disease is a major contributor to patient illness and mortality. It also is a primary driver of health care expenditure, costing more than $326 billion each year in the United States. Hypertension, or high blood pressure, is a major cardiovascular disorder that is estimated to affect over 50 million people in the United Sates alone. Of those with hypertension, it is reported that fewer than 30% have their blood pressure under control. Hypertension is a leading cause of heart failure and stroke. It is the primary cause of death in over 42,000 patients per year and is listed as a primary or contributing cause of death in over 200,000 patients per year in the U.S. Accordingly, hypertension is a serious health problem demanding significant research and development for the treatment thereof.

Hypertension occurs when the body's smaller blood vessels (arterioles) constrict, causing an increase in blood pressure. Because the blood vessels constrict, the heart must work harder to maintain blood flow at the higher pressures. Although the body may tolerate short periods of increased blood pressure, sustained hypertension may eventually result in damage to multiple body organs, including the kidneys, brain, eyes and other tissues, causing a variety of maladies associated therewith. The elevated blood pressure may also damage the lining of the blood vessels, accelerating the process of atherosclerosis and increasing the likelihood that a blood clot may develop. This could lead to a heart attack and/or stroke. Sustained high blood pressure may eventually result in an enlarged and damaged heart (hypertrophy), which may lead to heart failure.

Heart failure is the final common expression of a variety of cardiovascular disorders, including ischemic heart disease. It is characterized by an inability of the heart to pump enough blood to meet the body's needs and results in fatigue, reduced exercise capacity and poor survival. It is estimated that approximately 5,000,000 people in the United States suffer from heart failure, directly leading to 39,000 deaths per year and contributing to another 225,000 deaths per year. It is also estimated that greater than 400,000 new cases of heart failure are diagnosed each year. Heart failure accounts for over 900,000 hospital admissions annually, and is the most common discharge diagnosis in patients over the age of 65 years. It has been reported that the cost of treating heart failure in the United States exceeds $20 billion annually. Accordingly, heart failure is also a serious health problem demanding significant research and development for the treatment and/or management thereof.

Heart failure results in the activation of a number of body systems to compensate for the heart's inability to pump sufficient blood. Many of these responses are mediated by an increase in the level of activation of the sympathetic nervous system, as well as by activation of multiple other neurohormonal responses. Generally speaking, this sympathetic nervous system activation signals the heart to increase heart rate and force of contraction to increase the cardiac output; it signals the kidneys to expand the blood volume by retaining sodium and water; and it signals the arterioles to constrict to elevate the blood pressure. The cardiac, renal and vascular responses increase the workload of the heart, further accelerating myocardial damage and exacerbating the heart failure state. Accordingly, it is desirable to reduce the level of sympathetic nervous system activation in order to stop or at least minimize this vicious cycle and thereby treat or manage the heart failure.

A number of drug treatments have been proposed for the management of hypertension, heart failure and other cardiovascular disorders. These include vasodilators to reduce the blood pressure and ease the workload of the heart, diuretics to reduce fluid overload, inhibitors and blocking agents of the body's neurohormonal responses, and other medicaments.

Various surgical procedures have also been proposed for these maladies. For example, heart transplantation has been proposed for patients who suffer from severe, refractory heart failure. Alternatively, an implantable medical device such as a ventricular assist device (VAD) may be implanted in the chest to increase the pumping action of the heart. Alternatively, an intra-aortic balloon pump (IABP) may be used for maintaining heart function for short periods of time, but typically no longer than one month. Other surgical procedures are available as well.

It has been known for decades that the wall of the carotid sinus, a structure at the bifurcation of the common carotid arteries, contains stretch receptors (baroreceptors) that are sensitive to the blood pressure. These receptors send signals via the carotid sinus nerve to the brain, which in turn regulates the cardiovascular system to maintain normal blood pressure (the baroreflex), in part through activation of the sympathetic nervous system. Electrical stimulation of the carotid sinus nerve (baropacing) has previously been proposed to reduce blood pressure and the workload of the heart in the treatment of high blood pressure and angina. For example, U.S. Pat. No. 6,073,048 to Kieval et al. discloses a baroreflex modulation system and method for activating the baroreflex arc based on various cardiovascular and pulmonary parameters.

Although each of these alternative approaches is beneficial in some ways, each of the therapies has its own disadvantages. For example, drug therapy is often incompletely effective. Some patients may be unresponsive (refractory) to medical therapy. Drugs often have unwanted side effects and may need to be given in complex regimens. These and other factors contribute to poor patient compliance with medical therapy. Drug therapy may also be expensive, adding to the health care costs associated with these disorders. Likewise, surgical approaches are very costly, may be associated with significant patient morbidity and mortality and may not alter the natural history of the disease. Baropacing also has not gained acceptance. Several problems with electrical carotid sinus nerve stimulation have been reported in the medical literature.

These include the invasiveness of the surgical procedure to implant the nerve electrodes, and postoperative pain in the jaw, throat, face and head during stimulation. In addition, it has been noted that high voltages sometimes required for nerve stimulation may damage the carotid sinus nerves. Accordingly, there continues to be a substantial and long felt need for new devices and methods for treating and/or managing high blood pressure, heart failure and their associated cardiovascular and nervous system disorders.

A particularly promising approach for activating baroreceptors and other blood vessel receptors would be to implant an electrode structure or other activating device in an artery or vein adjacent to the receptor. The electrode structure could be similar to an inner arterial stent or graft and could be modified to have the needed electrical contact components for electrically activating the receptor. Energizing the implanted electrode structure, however, presents a number of difficulties. In particular, it is undesirable to run leads to the electrode structure through the arterial lumen and/or through an arterial or to a lesser extent venous wall. Such connection is particularly challenging if the target baroreceptors or other receptors are at or near the carotid sinus.

For these reasons, it would be desirable to provide non-traumatic systems and methods for electrically activating electrode structures implanted in the vasculature, particularly the arterial vasculature, such as those implanted adjacent baroreceptors or other receptors. Such systems and methods should preferably provide for "wireless" connection of the implanted electrode structure with a control system or other driver located remotely from the electrode structure, typically being implanted at a location in the body away from the site where the electrode structure is implanted. In particular, it is desirable to reduce or eliminate the need to run cable, wires, or other conductors within a lumen to connect the electrode structure to a power source. It is still further desirable if such wireless connections could provide for efficient and reliable energy transfer. This is a particular problem with fully implanted systems which have a limited battery or other power source. The sum of these objectives will be met by the inventions described hereinafter.

BRIEF SUMMARY OF THE INVENTION

To address hypertension, heart failure and their associated cardiovascular and nervous system disorders, the present invention provides a number of devices, systems and methods by which the blood pressure, nervous system activity, and neurohormonal activity may be selectively and controllably regulated by activating baroreceptors. By selectively and controllably activating baroreceptors, the present invention reduces excessive blood pressure, sympathetic nervous system activation and neurohormonal activation, thereby minimizing their deleterious effects on the heart, vasculature and other organs and tissues.

The present invention provides systems and methods for treating a patient by inducing a baroreceptor signal to effect a change in the baroreflex system (e.g., reduced heart rate, reduced blood pressure, etc.). The baroreceptor signal is activated or otherwise modified by selectively activating baroreceptors. To accomplish this, the system and method of the present invention utilize a baroreceptor activation device positioned near a baroreceptor in the carotid sinus, aortic arch, heart, common carotid arteries, subclavian arteries, brachiocephalic artery and/or other arterial and venous locations. Preferably, the baroreceptor activation device is located in the right and/or left carotid sinus (near the bifurcation of the common carotid artery) and/or the aortic arch. By way of example, not limitation, the present invention is described with reference to the carotid sinus location.

Generally speaking, the baroreceptor activation devices may be activated, deactivated or otherwise modulated to activate one or more baroreceptors and induce a baroreceptor signal or a change in the baroreceptor signal to thereby effect a change in the baroreflex system. The baroreceptor activation device may be activated, deactivated, or otherwise modulated continuously, periodically, or episodically. The baroreceptor activation device may comprise a wide variety of devices which utilize electrical (or in some instances electrically induced thermal or mechanical) to activate the baroreceptor. The baroreceptor may be activated directly, or activated indirectly via the adjacent vascular tissue. The baroreceptor activation device may be positioned at least in part inside the vascular lumen (i.e., intravascularly), outside the vascular wall (i.e., extravascularly) or within the vascular wall (i.e., intramurally).

In a particular aspect of the present invention, systems for inducing a baroreceptor signal to effect a change in the baroreflex system of a patient comprise a baroreceptor activation device and a control system. The baroreceptor activation device is positionable in, or in come cases on, a blood vessel, e.g., in a vascular lumen or over an outer surface of the blood vessel proximate a baroreceptor so that activation of the device can induce a baroreceptor signal in the baroreceptor. The control system is coupled to the baroreceptor activation device and includes a processor and a memory. The memory includes software defining a stimulus or activation regimen which can generate a control signal as a function of the regimen. The coupling between the baroreceptor activation device and the control system includes at least one wireless link between the device and the control system, the link usually but not necessarily being provided across a vascular wall. Alternately, direct wireless linkage between an implanted controller and an implanted activation device is sometimes preferred to reduce the need for tunneling to implant cables. The activation device typically comprises an antenna, coil, or the like, implanted in a blood vessel, adjacent a baroreceptor, and the control system typically comprises an antenna, coil, or the like, implantable at a site in the patient's body remote from the activation device, typically being located in a venous lumen adjacent to the arterial or venous implantation site of the activation device. Venous sites for coil or antenna implantation will usually be preferred.

In another aspect of the present invention, systems for activating vascular receptors comprise an extravascular transmitter and an electrode structure implantable in or over a blood vessel. The electrode structure is adapted to receive a signal transmitted from the extravascular transmitter and to produce electrical current in response thereto which activates the vascular receptor. The extravascular transmitter can have a variety of forms, such as an inductive coil, a radiofrequency transmitter, a microwave transmitter, or the like. The extravascular transmitter is usually adapted to be implanted in the patient's body, typically in a vein adjacent to a target receptor in an artery. In the case of venous implantation, the transmitter may comprise an antenna to be located adjacent the arterial site and a cable adapted to pass through the venous lumen to a remote penetration. The cable is useful for connecting the transmitter to a control system. The control system typically includes a driver which generates a control signal to be coupled to the extravascular transmitter. The control system will usually, although not necessarily, also be implantable, typically at a remote location or it may be connected to the transmitter via the cable.

The electrode structure may comprise a wide variety of forms, typically being a stent-like structure which may be intravascularly deployed, typically being delivered in a collapsed state and expanded or otherwise deployed at the implantation site near the target receptor. The electrode structure will usually comprise a conductive metal which can be energized by radio frequency (RE) or other electromagnetic (EM) transmission from the transmitter, and the conductive metal is preferably insulated over at least some surfaces. In particular, the electrode structure may comprise a (metal) receiving coil and may further comprise electrode pads connected to the receiving coil, where the electrode pads directly contact the internal vascular wall to activate the baroreceptors. Alternatively, extravascular electrode structures may find use as described in copending application Ser. No. 10/402,911, filed on Mar. 27, 2003, the full disclosure of which is incorporated herein by reference.

In a still further aspect of the present invention, a system for activating a baroreceptor in a carotid artery comprises an electrode structure and a transmitter. The electrode is deployable, usually implantable, or otherwise deployable in the carotid artery, typically near the carotid sinus in any of the common carotid artery, internal carotid artery, external carotid artery, or regions spanning therebetween. The electrode structure typically comprises a receiving coil, and the transmitter typically comprises a transmitting coil. The transmitting coil or antenna delivers EM energy to the receiving coil or structure and a responsive current is generated to activate the baroreceptor. Preferably, the system further comprises a control system which produces the EM control signal. The control system is connected to the transmitter implanted in the jugular vein by leads which pass through the lumen of the jugular vein and are connected to the control system via remote entry site. The control system is also preferably implantable at or near the remote entry site.

In a still further aspect of the present invention, methods for activating a vascular receptor comprise transmitting a control signal from an extravascular location, where the control signal is received by an electrode structure implanted in or on a blood vessel. The site of implantation of the electrode structure is adjacent to the vascular receptor, and the control signal induces electrical current in the electrode structure which can activate the receptor. The control signal is preferably transmitted from a vein adjacent to the vascular receptor. The control signal is preferably generated by a control system implanted remotely from the vascular receptor, where the control system is wired through a venous (or in some cases arterial) lumen to a transmitter in a vein (or artery) adjacent to the target vascular receptor.

In yet another aspect of the present invention, methods for implanting an electrode structure in an artery comprise intravascularly positioning the electrode structure at the target location in the artery, typically using intravascular implantation procedures of the type employed with the implantation of arterial stents and grafts. At least one electrical lead is advanced through a lumen of a vein adjacent to the arterial location of the electrode structure. The at least one lead may then be connected to the electrode structure in the artery by passing the lead through the arterial and venous walls. Such connections are preferably formed using an intravenous catheter having one or more stylets for penetrating the vascular walls and for threading and connecting the leads to the implanted electrode structure.

BRIEF DESCRIPTION OF THE DRAWINGS

FIGS. 5A-5C are schematic illustrations of baroreceptor activation devices in the form of an internal conductive structure, activated by an adjacent inductor, which electrically or thermally induces a baroreceptor signal in accordance with embodiments of the present invention. In FIGS. 5A and 5B, a transmitting coil is located remotely from an implanted control system, while in FIG. 5C, the transmitting coil or other antenna is located in the implanted control system itself.

FIGS. 6A and 6B are schematic illustrations of a baroreceptor activation device in the form of an internal conductive structure, activated by an internal inductor located in an adjacent vessel, which electrically or thermally induces a baroreceptor signal in accordance with an embodiment of the present invention.

FIGS. 7A and 7B are schematic illustrations of a baroreceptor activation device in the form of an internal conductive structure, activated by an external (skin mounted) inductor, which electrically or thermally induces a baroreceptor signal in accordance with an embodiment of the present invention.

FIGS. 9A-9C are schematic illustrations of a preferred embodiment of an inductively activated electrically conductive structure.

FIGS. 19A and 19C, illustrate alternative wireless transmission arrangements.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
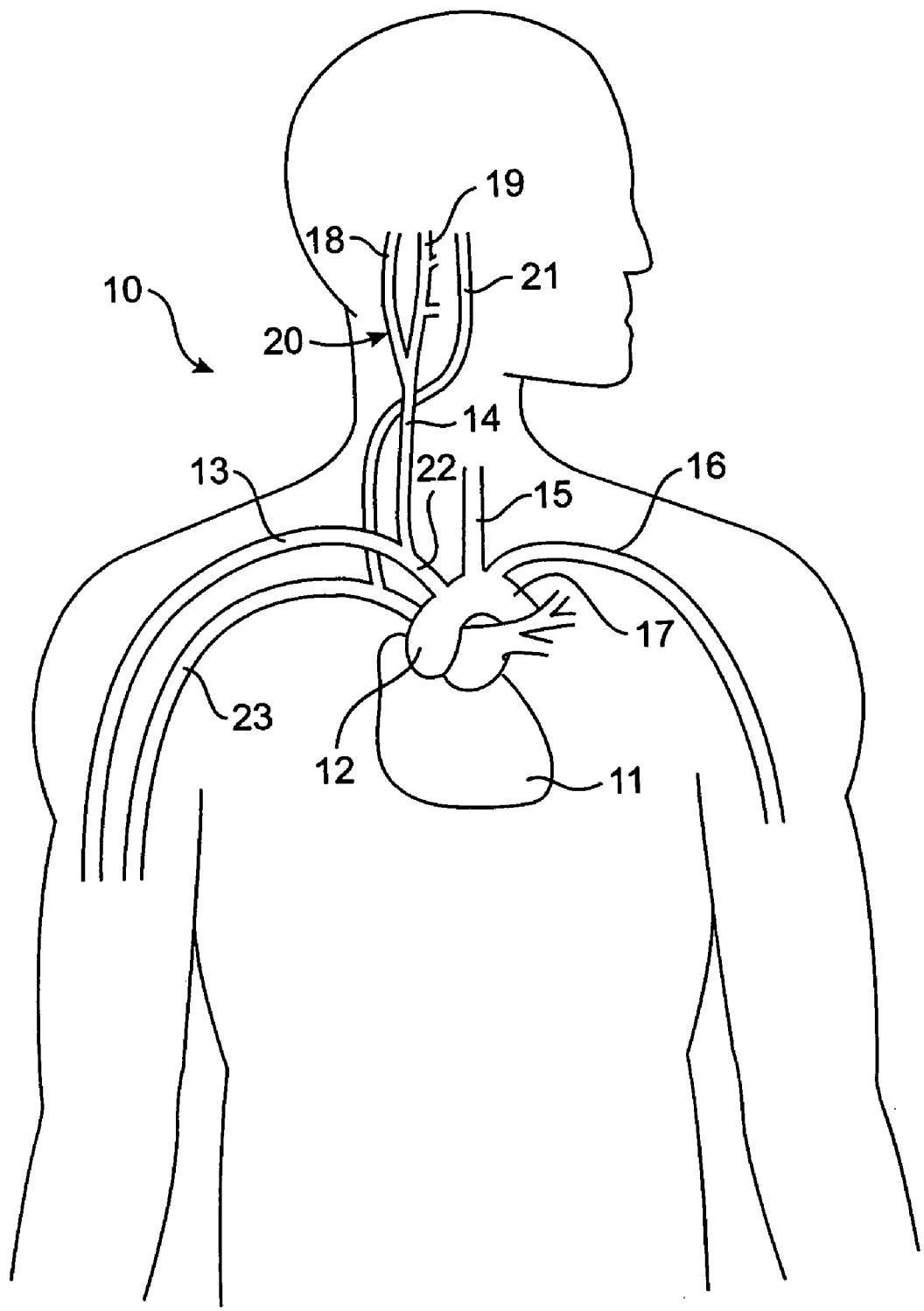
FIG. 1 is a schematic illustration of the upper torso of a human body showing the major arteries and veins and associated anatomy.

To better understand the present invention, it may be useful to explain some of the basic vascular anatomy associated with the cardiovascular system. Refer to FIG. 1 which is a schematic illustration of the upper torso of a human body 10 showing some of the major arteries and veins of the cardiovascular system. The left ventricle of the heart 11 pumps oxygenated blood up into the aortic arch 12. The right subclavian artery 13, the right common carotid artery 14, the left common carotid artery 15 and the left subclavian artery 16 branch off the aortic arch 12 proximal of the descending thoracic aorta 17. Although relatively short, a distinct vascular segment referred to as the brachiocephalic artery 22 connects the right subclavian artery 13 and the right common carotid artery 14 to the aortic arch 12. The right carotid artery 14 bifurcates into the right external carotid artery 18 and the right internal carotid artery 19 at the right carotid sinus 20. Although not shown for purposes of clarity only, the left carotid artery 15 similarly bifurcates into the left external carotid artery and the left internal carotid artery at the left carotid sinus.

From the aortic arch 12, oxygenated blood flows into the carotid arteries 18/19 and the subclavian arteries 13/16. From the carotid arteries 18/19, oxygenated blood circulates through the head and cerebral vasculature and oxygen depleted blood returns to the heart 11 by way of the jugular veins, of which only the right internal jugular vein 21 is shown for sake of clarity. From the subclavian arteries 13/16, oxygenated blood circulates through the upper peripheral vasculature and oxygen depleted blood returns to the heart by way of the subclavian veins, of which only the right subclavian vein 23 is shown, also for sake of clarity. The heart 11 pumps the oxygen depleted blood through the pulmonary system where it is re-oxygenated. The re-oxygenated blood returns to the heart 11 which pumps the re-oxygenated blood into the aortic arch as described above, and the cycle repeats.

Figure 2:
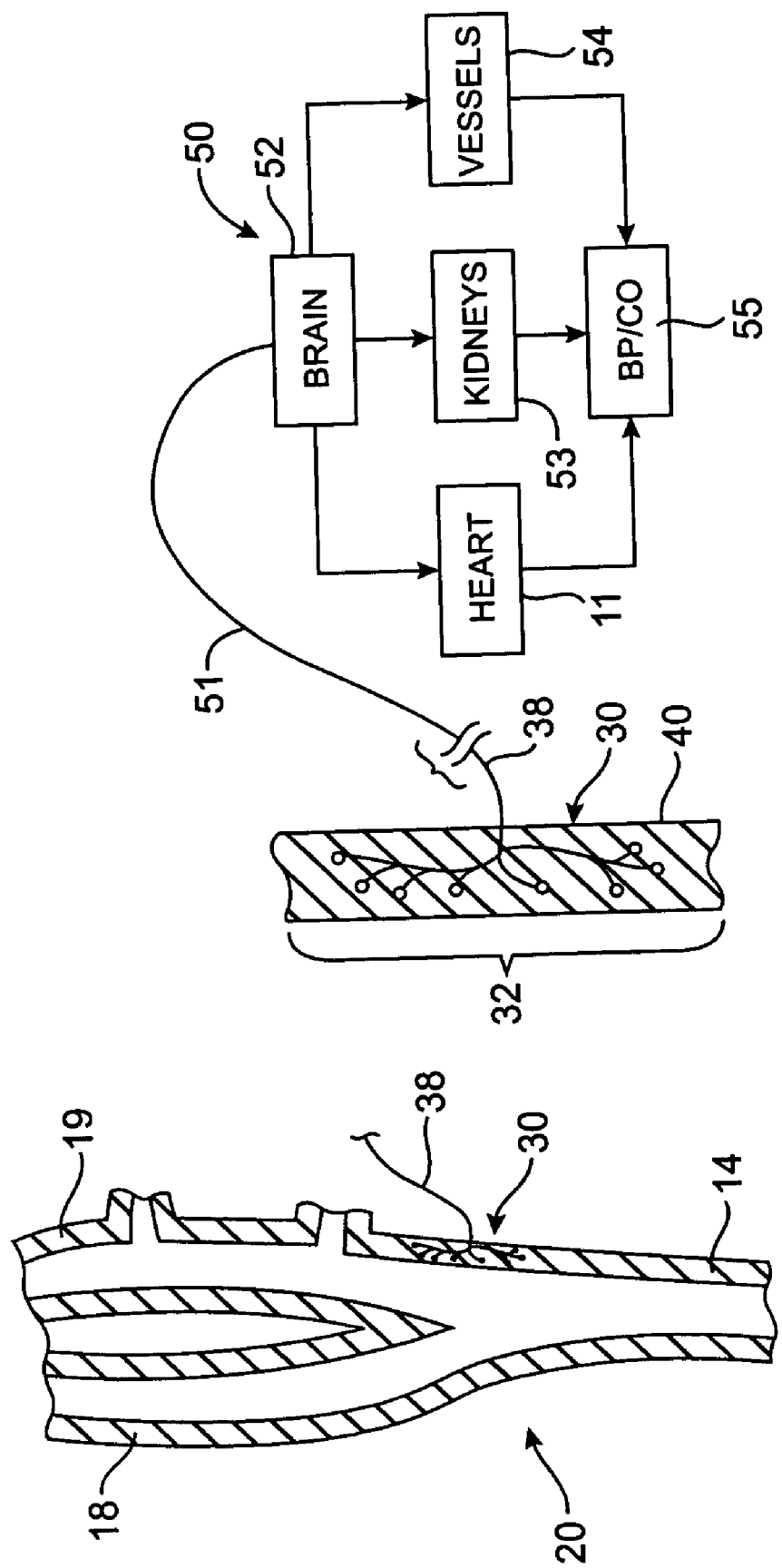
FIG. 2A is a cross-sectional schematic illustration of the carotid sinus and baroreceptors within the vascular wall.
FIG. 2B is a schematic illustration of baroreceptors within the vascular wall and the baroreflex system.

Within the arterial walls of the aortic arch 12, common carotid arteries 14/15 (near the right carotid sinus 20 and left carotid sinus), subclavian arteries 13/16 and brachiocephalic artery 22 there are baroreceptors 30. For example, as best seen in FIG. 2A, baroreceptors 30 reside within the vascular walls of the carotid sinus 20. Baroreceptors 30 are a type of stretch receptor used by the body to sense blood pressure. An increase in blood pressure causes the arterial wall to stretch, and a decrease in blood pressure causes the arterial wall to return to its original size. Such a cycle is repeated with each beat of the heart. Because baroreceptors 30 are located within the arterial wall, they are able to sense deformation of the adjacent tissue, which is indicative of a change in blood pressure. The baroreceptors 30 located in the right carotid sinus 20, the left carotid sinus and the aortic arch 12 play the most significant role in sensing blood pressure that affects the baroreflex system 50, which is described in more detail with reference to FIG. 2B.

Refer now to FIG. 2B, which shows a schematic illustration of baroreceptors 30 disposed in a generic vascular wall 40 and a schematic flow chart of the baroreflex system 50. Baroreceptors 30 are profusely distributed within the arterial walls 40 of the major arteries discussed previously, and generally form an arbor 32. The baroreceptor arbor 32 comprises a plurality of baroreceptors 30, each of which transmits baroreceptor signals to the brain 52 via nerve 38. The baroreceptors 30 are so profusely distributed and arborized within the vascular wall 40 that discrete baroreceptor arbors 32 are not readily discernable. To this end, those skilled in the art will appreciate that the baroreceptors 30 shown in FIG. 2B are primarily schematic for purposes of illustration and discussion.

Baroreceptor signals are used to activate a number of body systems which collectively may be referred to as the baroreflex system 50. Baroreceptors 30 are connected to the brain 52 via the nervous system 51. Thus, the brain 52 is able to detect changes in blood pressure, which is indicative of cardiac output. If cardiac output is insufficient to meet demand (i.e., the heart 11 is unable to pump sufficient blood), the baroreflex system 50 activates a number of body systems, including the heart 11, kidneys 53, vessels 54, and other organs/tissues. Such activation of the baroreflex system 50 generally corresponds to an increase in neurohormonal activity. Specifically, the baroreflex system 50 initiates a neurohormonal sequence that signals the heart 11 to increase heart rate and increase contraction force in order to increase cardiac output, signals the kidneys 53 to increase blood volume by retaining sodium and water, and signals the vessels 54 to constrict to elevate blood pressure. The cardiac, renal and vascular responses increase blood pressure and cardiac output 55, and thus increase the workload of the heart 11. In a patient with heart failure, this further accelerates myocardial damage and exacerbates the heart failure state.

To address the problems of hypertension, heart failure, other cardiovascular disorders and renal disorders, the present invention basically provides a number of devices, systems and methods by which the baroreflex system 50 is activated to reduce excessive blood pressure, autonomic nervous system activity and neurohormonal activation. In particular, the present invention provides a number of devices, systems and methods by which baroreceptors 30 may be activated, thereby indicating an increase in blood pressure and signaling the brain 52 to reduce the body's blood pressure and level of sympathetic nervous system and neurohormonal activation, and increase parasypathetic nervous system activation, thus having a beneficial effect on the cardiovascular system and other body systems.

Figure 3:
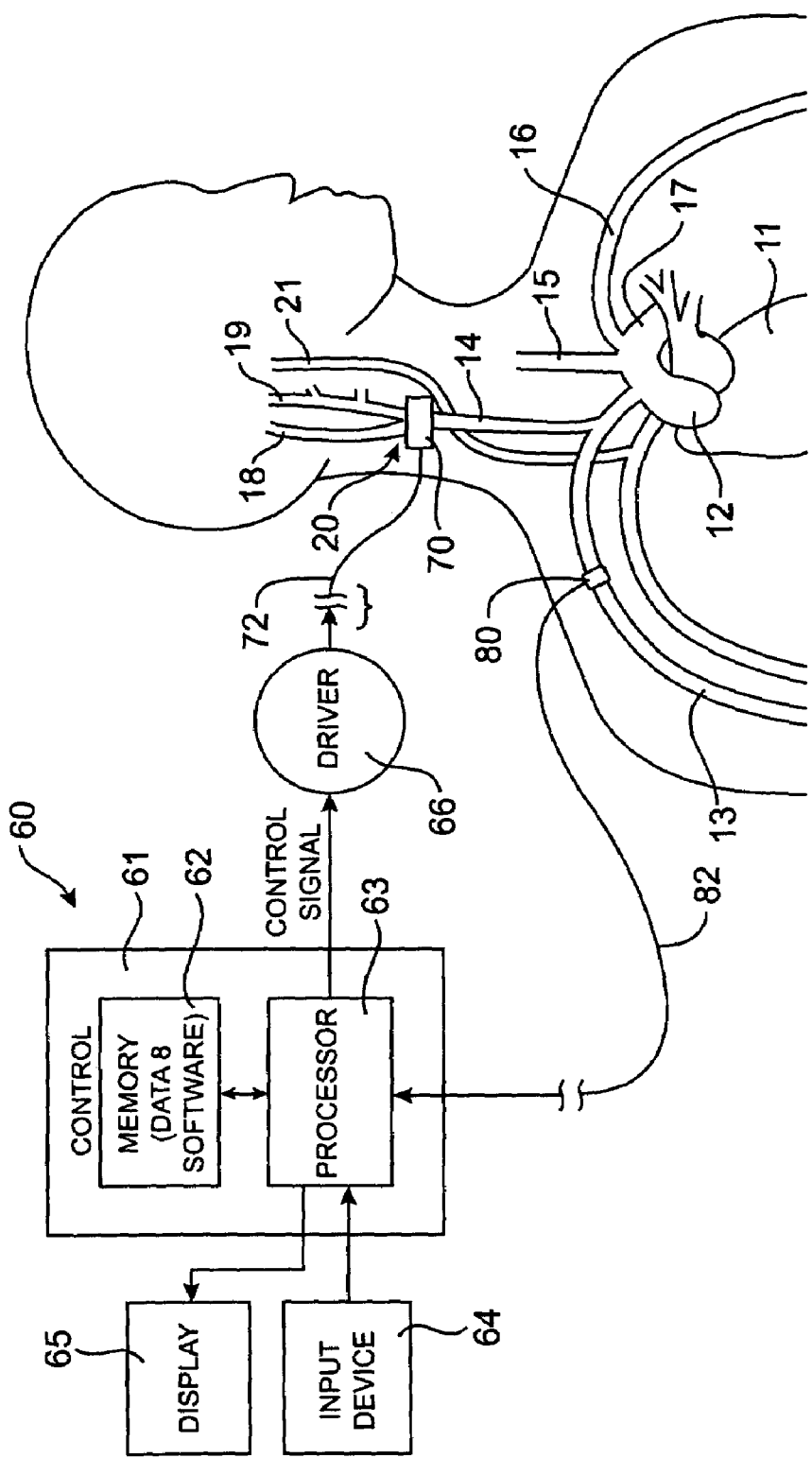
FIG. 3 is a schematic illustration of a baroreceptor activation system in accordance with the present invention.

With reference to FIG. 3, the present invention generally provides a system including a control system 60, a baroreceptor activation device 70, and a sensor 80 (optional), which generally operate in the following manner. The sensor 80 optionally senses and/or monitors a parameter (e.g., cardiovascular function) indicative of the need to modify the baroreflex system and generates a signal indicative of the parameter. In some embodiments (not shown), the sensor 80 may be incorporated into the structure of the activation device 70. The control system 60 generates a control signal as a function of the received sensor signal. The control signal activates, deactivates or otherwise modulates the baroreceptor activation device 70. Typically, activation of the device 70 results in activation of the baroreceptors 30. Alternatively, deactivation or modulation of the baroreceptor activation device 70 may cause or modify activation of the baroreceptors 30. The baroreceptor activation device 70 may comprise a wide variety of devices which utilize mechanical, electrical, thermal, chemical, biological, or other means to activate baroreceptors 30. Thus, when the sensor 80 detects a parameter indicative of the need to modify the baroreflex system activity (e.g., excessive blood pressure), the control system 60 generates a control signal to modulate (e.g. activate) the baroreceptor activation device 70 thereby inducing a baroreceptor 30 signal that is perceived by the brain 52 to be apparent excessive blood pressure. When the sensor 80 detects a parameter indicative of normal body function (e.g., normal blood pressure), the control system 60 generates a control signal to modulate (e.g., deactivate) the baroreceptor activation device 70.

The baroreceptor activation device 70 may directly activate one or more baroreceptors 30 by changing the electrical potential across the baroreceptors 30. It is also possible that changing the electrical potential might indirectly change the thermal or chemical potential across the tissue surrounding the baroreceptors 30 and/or otherwise may cause the surrounding tissue to stretch or otherwise deform, thus mechanically activating the baroreceptors 30.

The baroreceptor activation device 70 are suitable for implantation, and are preferably implanted using a minimally invasive percutaneous transluminal approach and/or a minimally invasive surgical approach. The baroreceptor activation device 70 may be positioned anywhere baroreceptors 30 effecting the baroreflex system 50 are numerous, such as in the heart 11, in the aortic arch 12, in the common carotid arteries 18/19 near the carotid sinus 20, in the subclavian arteries 13/16, or in the brachiocephalic artery 22. The baroreceptor activation device 70 may be implanted such that the device 70 is positioned immediately adjacent the baroreceptors 30. Alternatively, the baroreceptor activation device 70 may be outside the body such that the device 70 is positioned a short distance from but proximate to the baroreceptors 30. Preferably, the baroreceptor activation device 70 is implanted near the right carotid sinus 20 and/or the left carotid sinus (near the bifurcation of the common carotid artery) and/or the aortic arch 12, where baroreceptors 30 have a significant impact on the baroreflex system 50. For purposes of illustration only, the present invention is described with reference to baroreceptor activation device 70 positioned near the carotid sinus 20.

The optional sensor 80 is operably coupled to the control system 60 by electric sensor cable or lead 82. Optionally, the sensor could be coupled "wirelessly" and/or could be located on the activation device 70. The sensor 80 may comprise any suitable device that measures or monitors a parameter indicative of the need to modify the activity of the baroreflex system. For example, the sensor 80 may comprise a physiologic transducer or gauge that measures ECG, blood pressure (systolic, diastolic, average or pulse pressure), blood volumetric flow rate, blood flow velocity, blood pH, O2 or CO2 content, mixed venous oxygen saturation (SVO2), vasoactivity, nerve activity, tissue activity or composition. Examples of suitable transducers or gauges for the sensor 80 include ECG electrodes, a piezoelectric pressure transducer, an ultrasonic flow velocity transducer, an ultrasonic volumetric flow rate transducer, a thermodilution flow velocity transducer, a capacitive pressure transducer, a membrane pH electrode, an optical detector (SVO2) or a strain gage. Although only one sensor 80 is shown, multiple sensors 80 of the same or different type at the same or different locations may be utilized.

An example of an implantable blood pressure measurement device that may be disposed about a blood vessel is disclosed in U.S. Pat. No. 6,106,477 to Miesel et al., the entire disclosure of which is incorporated herein by reference. An example of a subcutaneous ECG monitor is available from Medtronic under the trade name REVEAL ILR and is disclosed in PCT Publication No. WO 98/02209, the entire disclosure of which is incorporated herein by reference. Other examples are disclosed in U.S. Pat. Nos. 5,987,352 and 5,331,966, the entire disclosures of which are incorporated herein by reference. Examples of devices and methods for measuring absolute blood pressure utilizing an ambient pressure reference are disclosed in U.S. Pat. No. 5,810,735 to Halperin et al., U.S. Pat. No. 5,904,708 to Goedeke, and PCT Publication No. WO 00/16686 to Brockway et al., the entire disclosures of which are incorporated herein by reference. The sensor 80 described herein may take the form of any of these devices or other devices that generally serve the same purpose.

The sensor 80 is preferably positioned in a chamber of the heart 11, or in/on a major artery such as the aortic arch 12, a common carotid artery 14/15, a subclavian artery 13/16 or the brachiocephalic artery 22, such that the parameter of interest may be readily ascertained. The sensor 80 may be disposed inside the body such as in or on an artery, a vein or a nerve (e.g. vagus nerve), or disposed outside the body, depending on the type of transducer or gauge utilized. The sensor 80 may be separate from the baroreceptor activation device 70 or combined therewith. For purposes of illustration only, the sensor 80 is shown positioned on the right subclavian artery 13.

By way of example, the control system 60 includes a control block 61 comprising a processor 63 and a memory 62. Control system 60 is connected to the sensor 80 by way of sensor cable 82. Control system 60 is also connected to the baroreceptor activation device 70 by way of electric control cable 72. Thus, the control system 60 receives a sensor signal from the sensor 80 by way of sensor cable 82, and transmits a control signal to the baroreceptor activation device 70 by way of control cable 72.

The system components 60/70/80 may be directly linked via cables 72/82 or by indirect means such as RF signal transceivers, ultrasonic transceivers or galvanic couplings. Examples of such indirect interconnection devices are disclosed in U.S. Pat. No. 4,987,897 to Funke and U.S. Pat. No. 5,113,859 to Funke, the entire disclosures of which are incorporated herein by reference.

The memory 62 may contain data related to the sensor signal, the control signal, and/or values and commands provided by the input device 64. The memory 62 may also include software containing one or more algorithms defining one or more functions or relationships between the control signal and the sensor signal. The algorithm may dictate activation or deactivation control signals depending on the sensor signal or a mathematical derivative thereof. The algorithm may dictate an activation or deactivation control signal when the sensor signal falls below a lower predetermined threshold value, rises above an upper predetermined threshold value or when the sensor signal indicates a specific physiologic event.

The algorithm may dynamically alter the threshold value as determined by the sensor input values.

As mentioned previously, the baroreceptor activation device 70 activates baroreceptors 30 electrically, optionally in combination with mechanical, thermal, chemical, biological or other co-activation. In some instances, the control system 60 includes a driver 66 to provide the desired power mode for the baroreceptor activation device 70. For example, the driver 66 may comprise a power amplifier or the like and the cable 72 may comprise electrical lead(s). In other instances, the driver 66 may not be necessary, particularly if the processor 63 generates a sufficiently strong electrical signal for low level electrical actuation of the baroreceptor activation device 70.

The control system 60 may operate as a closed loop utilizing feedback from the sensor 80, or other sensors, such as heart rate sensors which may be incorporated on the electrode assembly, or as an open loop utilizing reprogramming commands received by input device 64. The closed loop operation of the control system 60 preferably utilizes some feedback from the transducer 80, but may also operate in an open loop mode without feedback. Programming commands received by the input device 64 may directly influence the control signal, the output activation parameters, or may alter the software and related algorithms contained in memory 62. The treating physician and/or patient may provide commands to input device 64. Display 65 may be used to view the sensor signal, control signal and/or the software/data contained in memory 62.

The control signal generated by the control system 60 may be continuous, periodic, alternating, episodic or a combination thereof, as dictated by an algorithm contained in memory 62. Continuous control signals include a constant pulse, a constant train of pulses, a triggered pulse and a triggered train of pulses. Examples of periodic control signals include each of the continuous control signals described above which have a designated start time (e.g., beginning of each period as designated by minutes, hours, or days in combinations of) and a designated duration (e.g., seconds, minutes, hours, or days in combinations of). Examples of alternating control signals include each of the continuous control signals as described above which alternate between the right and left output channels. Examples of episodic control signals include each of the continuous control signals described above which are triggered by an episode (e.g., activation by the physician/patient, an increase/decrease in blood pressure above a certain threshold, heart rate above/below certain levels, etc.).

The stimulus regimen governed by the control system 60 may be selected to promote long term efficacy. It is theorized that uninterrupted or otherwise unchanging activation of the baroreceptors 30 may result in the baroreceptors and/or the baroreflex system becoming less responsive over time, thereby diminishing the long term effectiveness of the therapy. Therefore, the stimulus regimen maybe selected to activate, deactivate or otherwise modulate the baroreceptor activation device 70 in such a way that therapeutic efficacy is maintained for months, preferably for years.

In addition to maintaining therapeutic efficacy over time, the stimulus regimens of the present invention may be selected reduce power requirement/consumption of the system 60. As will be described in more detail hereinafter, the stimulus regimen may dictate that the baroreceptor activation device 70 be initially activated at a relatively higher energy and/or power level, and subsequently activated at a relatively lower energy and/or power level. The first level attains the desired initial therapeutic affect, and the second (lower) level sustains the desired therapeutic affect long term. By reducing the energy and/or power levels after the desired therapeutic affect is initially attained, the energy required or consumed by the activation device 70 is also reduced long term. This may correlate into systems having greater longevity and/or reduced size (due to reductions in the size of the power supply and associated components).

A first general approach for a stimulus regimen which promotes long term efficacy and reduces power requirements/consumption involves generating a control signal to cause the baroreceptor activation device 70 to have a first output level of relatively higher energy and/or power, and subsequently changing the control signal to cause the baroreceptor activation device 70 to have a second output level of relatively lower energy and/or power. The first output level may be selected and maintained for sufficient time to attain the desired initial affect (e.g., reduced heart rate and/or blood pressure), after which the output level may be reduced to the second level for sufficient time to sustain the desired affect for the desired period of time.

For example, if the first output level has a power and/or energy value of X1, the second output level may have a power and/or energy value of X2, wherein X2 is less than X1. In some instances, X2 may be equal to zero, such that the first level is "on" and the second level is "off". It is recognized that power and energy refer to two different parameters, and in some cases, a change in one of the parameters (power or energy) may not correlate to the same or similar change in the other parameter. In the present invention, it is contemplated that a change in one or both of the parameters may be suitable to obtain the desired result of promoting long term efficacy.

It is also contemplated that more than two levels may be used. Each further level may increase the output energy or power to attain the desired affect, or decrease the output energy or power to retain the desired affect. For example, in some instances, it may be desirable to have further reductions in the output level if the desired affect may be sustained at lower power or energy levels. In other instances, particularly when the desired affect is diminishing or is otherwise not sustained, it may be desirable to increase the output level until the desired affect is reestablished, and subsequently decrease the output level to sustain the affect.

The transition from each level may be a step function (e.g., a single step or a series of steps), a gradual transition over a period of time, or a combination thereof. In addition, the signal levels may be continuous, periodic, alternating, or episodic as discussed previously.

In electrical activation using a non-modulated signal, the output (power or energy) level of the baroreceptor activation device 70 may be changed by adjusting the output signal voltage level, current level and/or signal duration. The output signal of the baroreceptor activation device 70 may be, for example, constant current or constant voltage. In electrical activation embodiments using a modulated signal, wherein the output signal comprises, for example, a series of pulses, several pulse characteristics may be changed individually or in combination to change the power or energy level of the output signal. Such pulse characteristics include, but are not limited to: pulse amplitude (PA), pulse frequency (PF), pulse width or duration (PW), pulse waveform (square, triangular, sinusoidal, etc.), pulse polarity and pulse phase (monophasic, biphasic), and sequential.

In electrical activation wherein the output signal comprises a pulse train, several other signal characteristics may be changed in addition to the pulse characteristics described above, as described in copending application Ser. No. 09/964,079, the full disclosure of which is incorporated herein by reference.

The control system 60 may be implanted in whole or in part. For example, the entire control system 60 may be carried externally by the patient utilizing transdermal connections to the sensor lead 82 and the control lead 72. Alternatively, the control block 61 and driver 66 may be implanted with the input device 64 and display 65 carried externally by the patient utilizing transdermal connections therebetween. As a further alternative, the transdermal connections may be replaced by cooperating transmitters/receivers to remotely communicate between components of the control system 60 and/or the sensor 80 and baroreceptor activation device 70.

With general reference to FIGS. 4-9, schematic illustrations of specific embodiments of the baroreceptor activation device 70 are shown. The design, function and use of these specific embodiments, in addition to the control system 60 and sensor 80 (not shown), are the same as described with reference to FIG. 3, unless otherwise noted or apparent from the description. In addition, the anatomical features illustrated in FIGS. 4-8 are the same as discussed with reference to FIGS. 1, 2A and 2B, unless otherwise noted. In each embodiment, the connections between the components 60/70/80 may be physical (e.g., wires, tubes, cables, etc.) or remote (e.g., transmitter/receiver, inductive, magnetic, etc.). For physical connections, the connection may travel intra-arterially, intravenously, subcutaneously, or through other natural tissue paths.

Figure 4B:
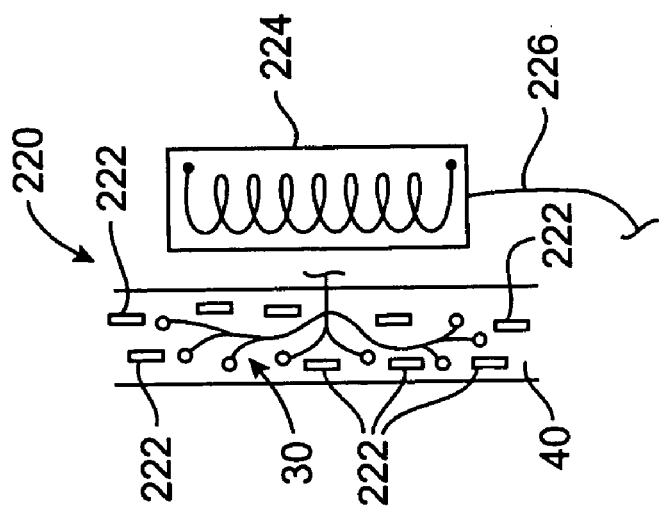
FIGS. 4A and 4B are schematic illustrations of a baroreceptor activation device which electro-mechanically induces a baroreceptor signal in accordance with an embodiment of the present invention.
Figure 4A:
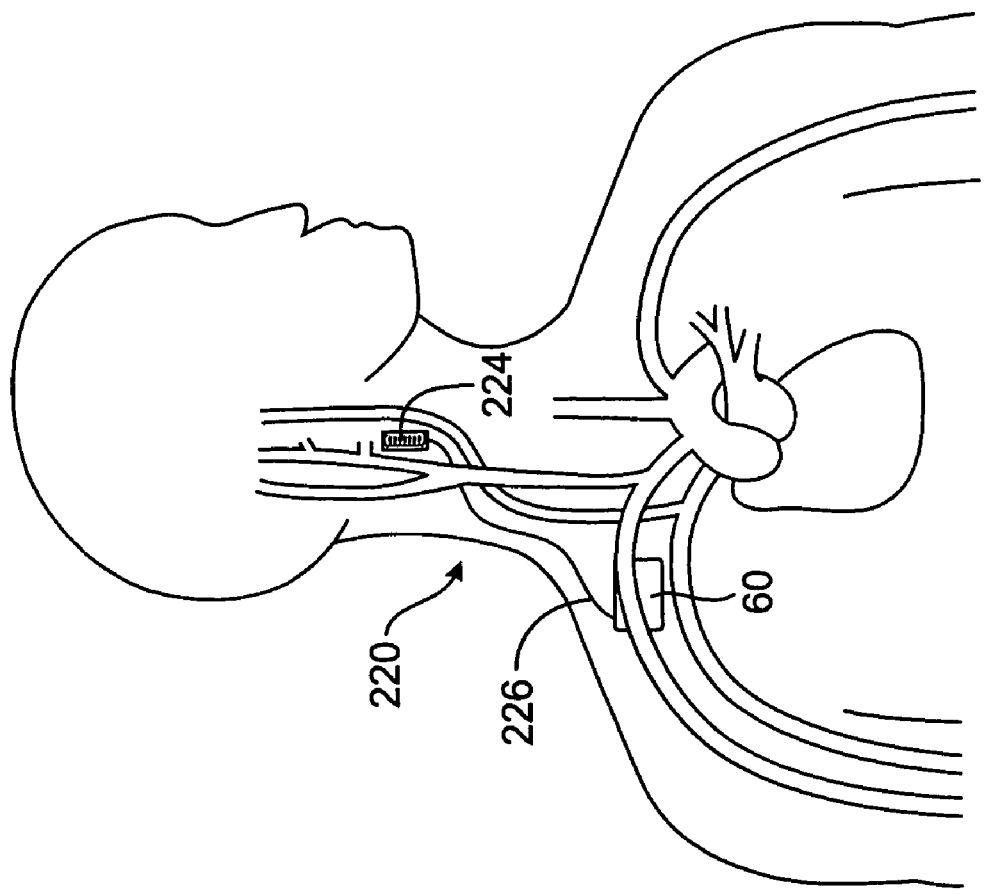

Refer now to FIGS. 4A and 4B which show schematic illustrations of a baroreceptor activation device 220 in the form of magnetic particles 222 disposed in the vascular wall 40. The magnetic particles 222 may comprise magnetically responsive materials (i.e., ferrous based materials) and may be magnetically neutral or magnetically active. Preferably, the magnetic particles 222 comprise permanent magnets having an elongate cylinder shape with north and south poles to strongly respond to magnetic fields. The magnetic particles 222 are actuated by an electromagnetic coil 224 which is operably coupled to the driver 66 of the control system 60 by way of an electrical cable 226. The electromagnetic coil 224 may be implanted as shown, or located outside the body, in which case the driver 66 and the remainder of the control system 60 would also be located outside the body. By selectively activating the electromagnetic coil 224 to create a magnetic field, the magnetic particles 222 may be repelled, attracted or rotated. Alternatively, the magnetic field created by the electromagnetic coil 224 may be alternated such that the magnetic particles 222 vibrate within the vascular wall 40. When the magnetic particles are repelled, attracted, rotated, vibrated or otherwise moved by the magnetic field created by the electromagnetic coil 224, the baroreceptors 30 are mechanically activated.

The electromagnetic coil 224 is preferably placed as close as possible to the magnetic particles 222 in the vascular wall 40, and may be placed intravascularly, extravascularly, or in any of the alternative locations discussed with reference to inductor shown in FIGS. 5-7. The magnetic particles 222 may be implanted in the vascular wall 40 by injecting a ferro-fluid or a ferro-particle suspension into the vascular wall adjacent to the baroreceptors 30. To increase biocompatibility, the particles 222 may be coated with a ceramic, polymeric or other inert material. Injection of the fluid carrying the magnetic particles 222 is preferably performed percutaneously.

Electrical activation signals may be indirectly delivered utilizing an inductor as illustrated in FIGS. 5-9. The embodiments of FIGS. 5-7 utilize an inductor 286 which is operably connected to the driver 66 of the control system 60 by way of electrical lead 284. The inductor 286 comprises an electrical winding which creates a magnetic field 287 (as seen in FIG. 9) around the electrode structure 282. The magnetic field 287 may be alternated by alternating the direction of current flow through the inductor 286. Accordingly, the inductor 286 may be utilized to create current flow in the electrode structure 282 to thereby deliver electrical signals to the vascular wall 40 to directly or indirectly activate the baroreceptors 30. In all embodiments, the inductor 286 may be covered with an electrically insulating material to eliminate direct electrical stimulation of tissues surrounding the inductor 286. A preferred embodiment of an inductively activated electrode structure 282 is described in more detail with reference to FIGS. 9A-9C.

Figure 5C:
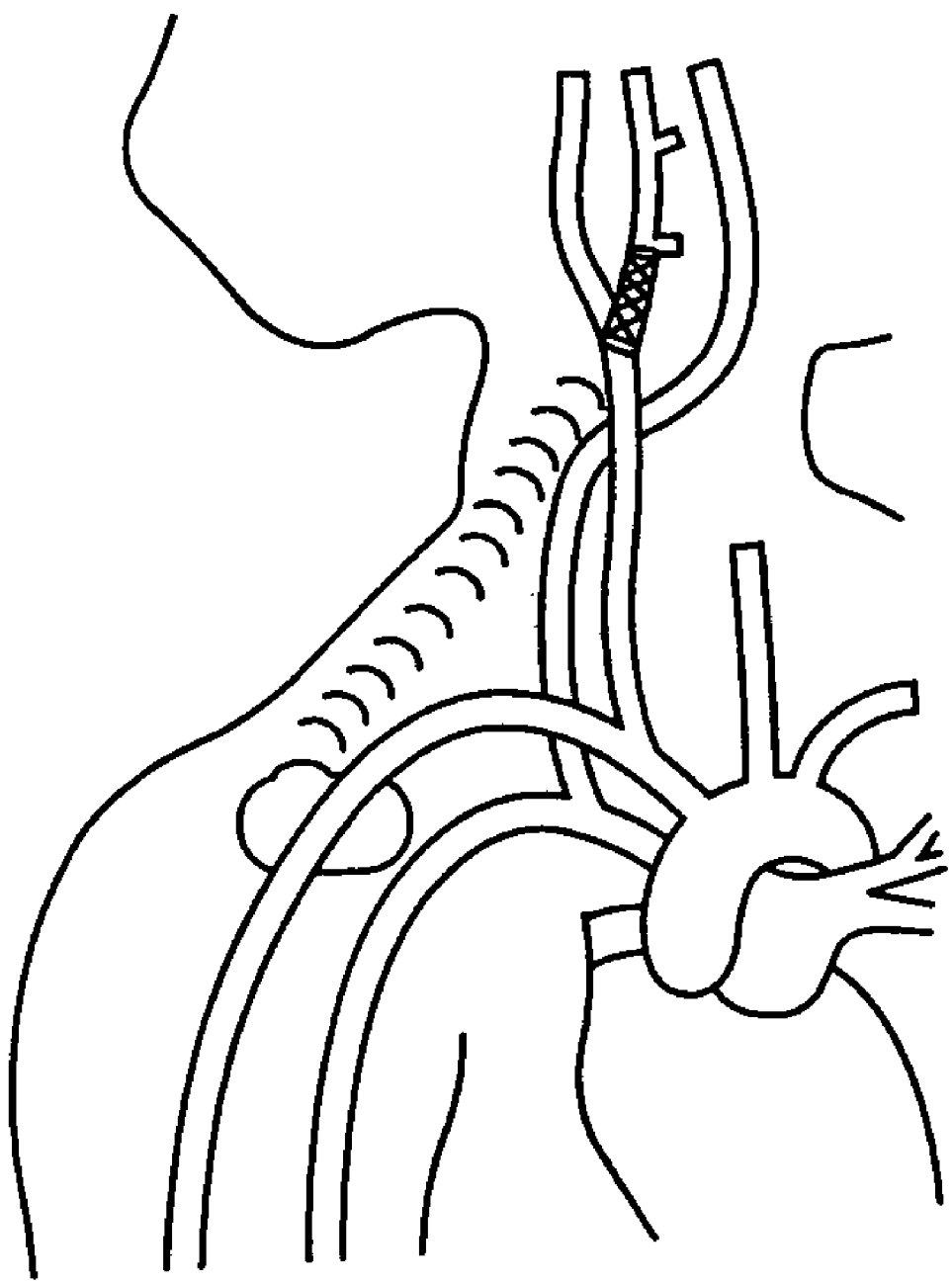

The embodiments of FIGS. 5-7 may be modified to form a cathode/anode arrangement. Specifically, the electrical inductor 286 would be connected to the driver 66 as shown in FIGS. 5-7 and the electrode structure 282 would be connected to the driver 66. With this arrangement, the electrode structure 282 and the inductor 286 may be any suitable geometry and need not be coiled for purposes of induction. The electrode structure 282 and the inductor 286 would comprise a cathode/anode or anode/cathode pair. For example, when activated, the cathode 282 may generate a primary stream of electrons which travel through the inter-electrode space (i.e., vascular tissue and baroreceptors 30) to the anode 286. The cathode is preferably cold, as opposed to thermionic, during electron emission. The electrons may be used to electrically or thermally activate the baroreceptors 30 as discussed previously.

Alternative means of indirect or wireless transmission of electrical energy are described in U.S. Pat. No. 6,231,516 to Keilman et al., the entire disclosure of which is hereby incorporated by reference. The therapeutic transducer disclosed by Keilman et al. may be replaced by electrode structure 282, electrodes 302 or electrodes 520, to which power may be delivered by the RF coupling coil system described by Keilman et al.

The electrical inductor 286 is preferably disposed as close as possible to the electrode structure 282. For example, the electrical inductor 286 may be disposed adjacent the vascular wall as illustrated in FIGS. 5A and 5B. Alternatively, the inductor 286 may be disposed in an adjacent vessel as illustrated in FIGS. 6A and 6B. If the electrode structure 282 is disposed in the carotid sinus 20, for example, the inductor 286 may be disposed in the internal jugular vein 21 as illustrated in FIGS. 6A and 6B. In the embodiment of FIGS. 6A and 6B, the electrical inductor 286 may comprise a similar structure as the electrode structure 282. As a further alternative, the electrical inductor 286 may be disposed outside the patient's body, but as close as possible to the electrode structure 282. If the electrode structure 282 is disposed in the carotid sinus 20, for example, the electrical inductor 286 may be disposed on the right or left side of the neck of the patient as illustrated in FIGS. 7A and 7B. In the embodiment of FIGS. 7A and 7B, wherein the electrical inductor 286 is disposed outside the patient's body, the control system 60 may also be disposed outside the patient's body.

In terms of implant location, the electrode structure 282 may be intravascularly disposed as described with reference to FIGS. 6A and 6B, or extravascularly disposed. Except as described herein, the extravascular electrode structure is the same in design, function, and use as the intravascular electrode structure 282. The electrode structure may comprise a coil, braid or other structure capable of surrounding the vascular wall. Alternatively, the electrode structure may comprise one or more electrode patches distributed around the outside surface of the vascular wall. Because the electrode structure is disposed on the outside surface of the vascular wall, intravascular delivery techniques may not be practical, but minimally invasive surgical techniques will suffice.

Figure 8B:
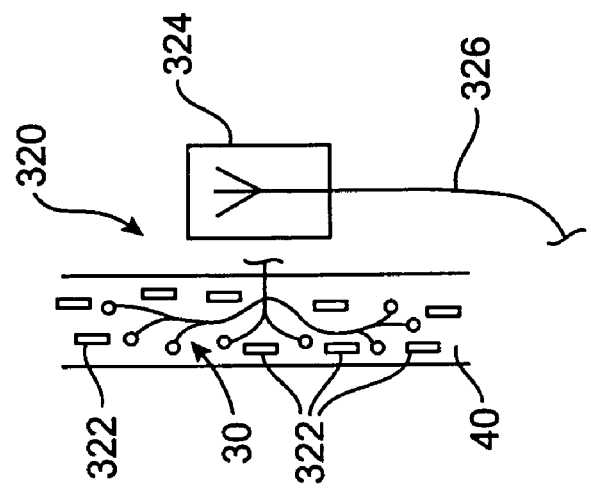
FIGS. 8A and 8B are schematic illustrations of an electromagnetic baroreceptor activation device which directly induces a baroreceptor signal via a thermal or electrical mechanism in accordance with an embodiment of the present invention.
Figure 8A:
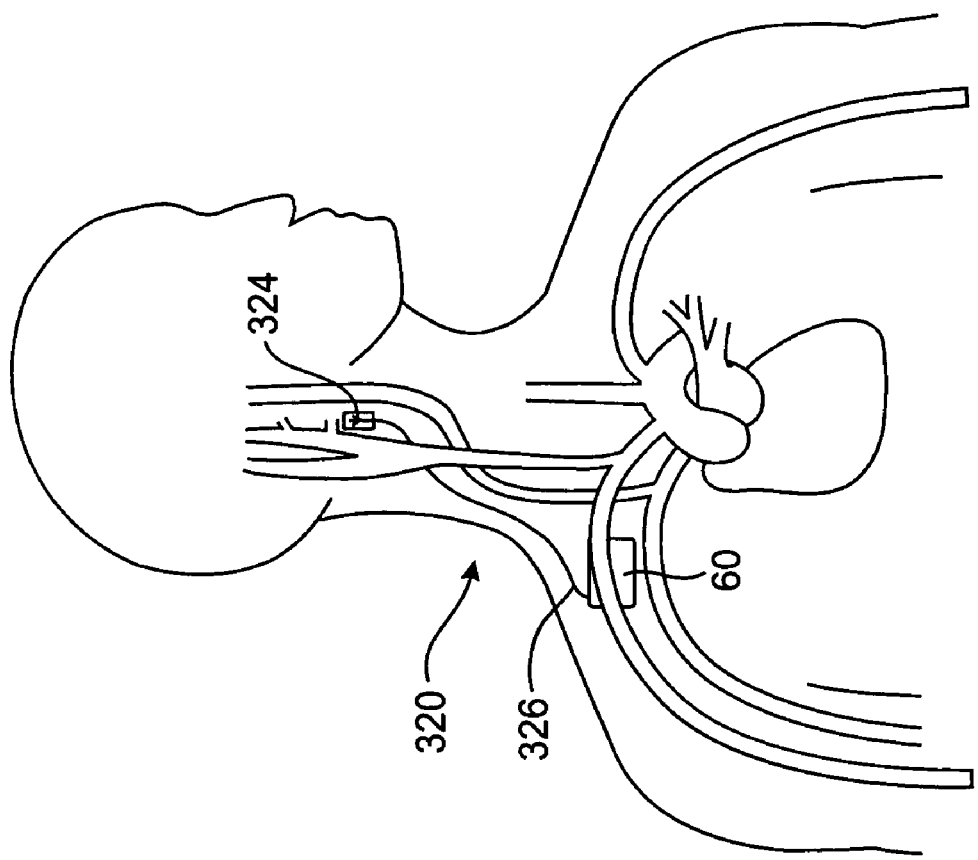

Refer now to FIGS. 8A and 8B which show schematic illustrations of a baroreceptor activation device 320 in the form of electrically conductive particles 322 disposed in the vascular wall. This embodiment is substantially the same as the embodiments described with reference to FIGS. 5-7, except that the electrically conductive particles 322 are disposed within the vascular wall, as opposed to the electrically conductive structures 288 which are disposed on either side of the vascular wall.

In this embodiment, the driver 66 of the control system 60 comprises an electromagnetic transmitter such as a radiofrequency or microwave transmitter. Electromagnetic radiation is created by the transmitter 66 which is operably coupled to an antenna 324 by way of electrical lead 326. Electromagnetic waves are emitted by the antenna 324 and received by the electrically conductive particles 322 disposed in the vascular wall 40. Electromagnetic energy creates oscillating current flow within the electrically conductive particles 322, and depending on the intensity of the electromagnetic radiation and the resistivity of the conductive particles 322, may cause the electrical particles 322 to generate heat. The electrical or thermal energy generated by the electrically conductive particles 322 may directly activate the baroreceptors 30, or indirectly activate the baroreceptors 30 by way of the surrounding vascular wall tissue.

The electromagnetic radiation transmitter 66 and antenna 324 may be disposed in the patient's body, with the antenna 324 disposed adjacent to the conductive particles in the vascular wall 40 as illustrated in FIGS. 8A and 8B. Alternatively, the antenna 324 may be disposed in any of the positions described with reference to the electrical inductor shown in FIGS. 5-7. It is also contemplated that the electromagnetic radiation transmitter 66 and antenna 324 may be utilized in combination with the intravascular and extravascular electrically conductive structures 282 (acting like heater coils) described with reference to FIGS. 5-7 to generate thermal energy on either side of the vascular wall.

As an alternative, the electromagnetic radiation transmitter 66 and antenna 324 may be used without the electrically conductive particles 322. Specifically, the electromagnetic radiation transmitter 66 and antenna 324 may be used to deliver electromagnetic radiation (e.g., RF, microwave) directly to the baroreceptors 30 or the tissue adjacent thereto to cause localized heating, thereby thermally inducing a baroreceptor 30 signal.

Refer now to FIGS. 9A-9C which show schematic illustrations of a specific embodiment of an inductively activated electrode structure 282 for use with the embodiments described with reference to FIGS. 5-7. In this embodiment, current flow in the electrode structure 282 is induced by a magnetic field 287 created by an inductor 286 which is operably coupled to the driver 66 of the control system 60 by way of electrical cable 284. The electrode structure 282 preferably comprises a multi-filar self-expanding braid structure including a plurality of individual members 282a, 282b, 282c and 282d. However, the electrode structure 282 may simply comprise a single coil for purposes of this embodiment.

Each of the individual coil members 282a-282d comprising the electrode structure 282 consists of a plurality of individual coil turns 281 connected end to end as illustrated in FIGS. 9B and 9C. FIG. 9C is a detailed view of the connection between adjacent coil turns 281 as shown in FIG. 9B. Each coil turn 281 comprises electrically isolated wires or receivers in which a current flow is established when a changing magnetic field 287 is created by the inductor 286. The inductor 286 is preferably covered with an electrically insulating material to eliminate direct electrical stimulation of tissues surrounding the inductor 286. Current flow through each coil turn 281 results in a potential drop 288 between each end of the coil turn 281. With a potential drop defined at each junction between adjacent coil turns 281, a localized current flow cell is created in the vessel wall adjacent each junction. Thus an array or plurality of bipoles are created by the electrode structure 282 and uniformly distributed around the vessel wall. Each coil turn 281 comprises an electrically conductive wire material 290 surrounded by an electrically insulating material 292. The ends of each coil turn 281 are connected by an electrically insulated material 294 such that each coil turn 281 remains electrically isolated. The insulating material 294 mechanically joins but electrically isolates adjacent coil turns 281 such that each turn 281 responds with a similar potential drop 288 when current flow is induced by the changing magnetic field 287 of the inductor 286. An exposed portion 296 is provided at each end of each coil turn 281 to facilitate contact with the vascular wall tissue. Each exposed portion 296 comprises an isolated electrode in contact with the vessel wall. The changing magnetic field 287 of the inductor 286 causes a potential drop in each coil turn 281 thereby creating small current flow cells in the vessel wall corresponding to adjacent exposed regions 296. The creation of multiple small current cells along the inner wall of the blood vessel serves to create a cylindrical zone of relatively high current density such that the baroreceptors 30 are activated. However, the cylindrical current density field quickly reduces to a negligible current density near the outer wall of the vascular wall, which serves to limit extraneous current leakage to minimize or eliminate unwanted activation of extravascular tissues and structures such as nerves or muscles.

Refer now to FIGS. 10-15 which illustrate variations on the intravascular baroreceptor activation device 280 and electrode structure 282 described previously. In the embodiments illustrated in FIGS. 10-15, the electrical baroreceptor activation devices comprise stent like structures that may be directly or wirelessly coupled to the control system 60 as described previously. In particular, wireless transmission of electrical energy may be employed as described in U.S. Pat. No. 6,231,516 to Keilman et al., the entire disclosure of which is hereby incorporated by reference. The stent like structures may comprise conventional intravascular stents that carry one or more electrodes and/or receiving coils, or a portion of the stent like structure may serve as one or more electrodes and/or receiving coils. The stent like structures may be intravascularly delivered in a collapsed state, and deployed to an expanded state in much the same way that intravascular stents are implanted in coronary and peripheral applications.

Figure 10:
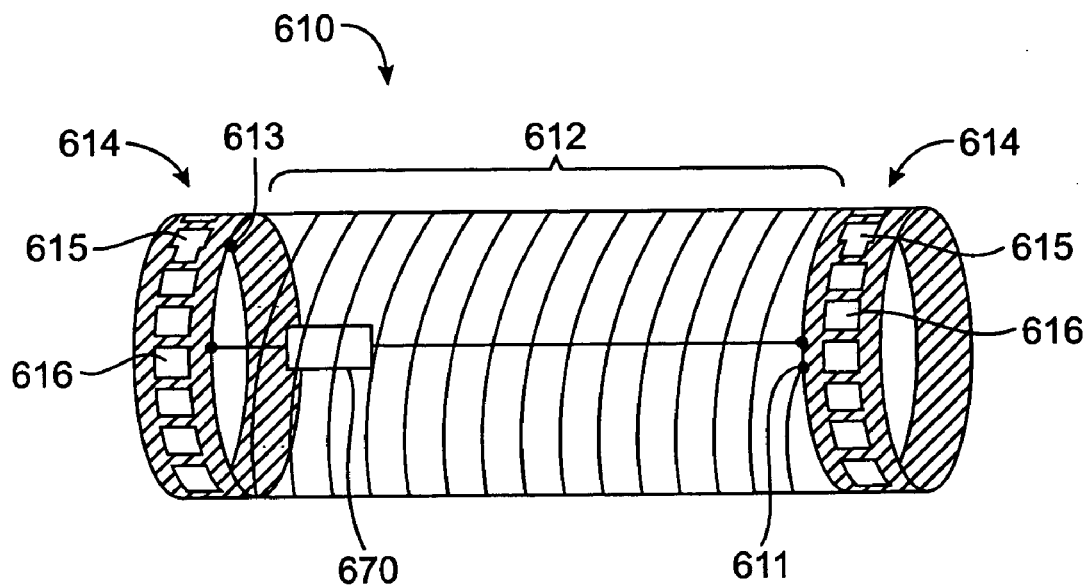
FIG. 10 illustrates an electrical intravascular baroreceptor activation device comprising a stent-like structure.

For example, in the embodiment illustrated in FIG. 10, the electrical intravascular baroreceptor activation device 610 comprises a stent like structure having a coil mid portion 612 and two ratcheting end portions 614. The coil mid portion 612 unwinds as the device 610 is deployed in the vessel lumen, and the ratcheting ends portions 614 selectively expand (self expanded or balloon expanded) to the desired diameter, with tabs 615 engaging openings 616 to lock the device 610 in the expanded state. Those skilled in the art will recognize that other stent like structures may be employed as well, such as self expanding stent structures.

In the embodiment of FIG. 10, the coil mid portion 612 may comprise an insulated conductive metal such as MP 35, SST, or a NiTi alloy, and may serve as an RF receiving coil which receives RF transmissions from an antenna or coupling coil (not shown) connected to the control system 60. In this embodiment, the winding axis of the coil 612 is common with the longitudinal center axis of the tubular device 610. The ratcheting end portions 614 may comprise a conductive material such as MP 35, SST, or a NiTi alloy, with the inside surface of the end portions 614 insulated and the outside surface of the end portions 614 at least partially uninsulated to serve as electrodes which contact the inside surface of the vessel wall. Alternatively, the end portions 614 may incorporate conductive barbs to serve as electrodes which extend into the vascular wall upon expansion of the device 610. One end 611 of the coil 612 is connected to one end portion 614, and the other end 613 of the coil 612 is connected to the other end portion 614. With this arrangement, a signal transmitted by control system 60 is received by the coil 612 and travels to inside surface of the vascular wall adjacent baroreceptors via the outside surface of the end portions 614. Optionally, an electronics module 670 may be electrically connected between the end portions 614 and mounted to the mid portion 612, for example. The electronics module 670 may comprise a tuning capacitor, for example, as will be described in more detail hereinafter.

Figure 11:
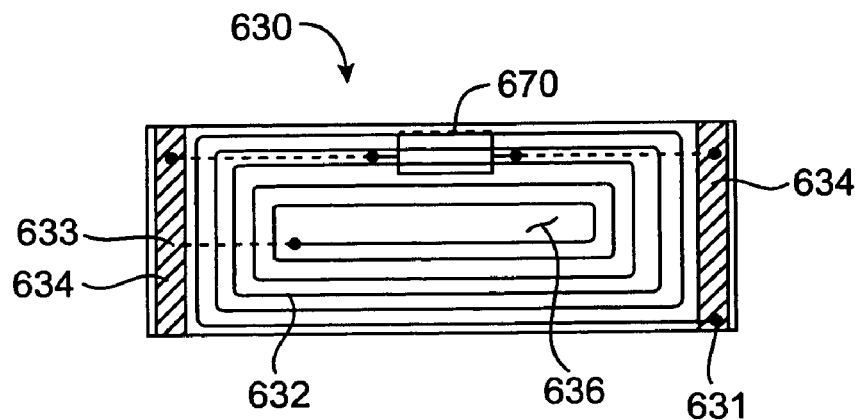
FIGS. 11 and 12 illustrate an electrical intravascular baroreceptor activation device including an electrode and receiving assembly wrapped or upon the outside surface of an intravascular stent.
Figure 12:
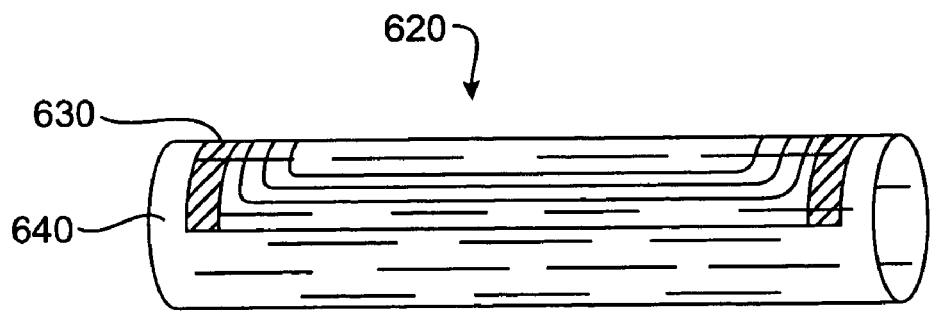

Refer now to FIGS. 11 and 12 which illustrate an electrical intravascular baroreceptor activation device 620, including an electrode and receiving coil assembly 630 wrapped about the outside surface of an intravascular stent 640. The electrode and receiving coil assembly 630 may be movably attached to the intravascular stent 640 to permit free expansion of the stent 640, and/or may be made expandable to permit expansion of the assembly 630 with expansion of the stent 640. Stent 640 may comprise a self expanding stent, a balloon expandable stent, or any of a wide variety of other types of intravascular stents known to those skilled in the art. In the embodiment illustrated, the stent 640 is shown in the form of a tubular metal stent having a plurality of slots.

The assembly 630 shown in FIG. 11 may be in the shape of a semi cylinder (shown) or tubular sleeve (not shown) and may include a receiving coil 632 and one or more electrode pads 634. The coil 632 and the pads 634 may comprise a conductive metal such as Pt or a Pt alloy disposed on a flex circuit substrate material 636 such as polyimide. The metal may be laminated on the flex circuit substrate 636 and may be chemically etched to define the pattern of the coil 632 and pads 634. One end 631 of the coil 632 is connected to one of the electrode pads 634, and the other end 633 of the coil 632 is connected via a backside tracer to the other electrode pad 634. With this arrangement, a signal transmitted by control system 60 is received by the coil 632 and travels to inside surface of the vascular wall adjacent baroreceptors via the electrode pads 634. An electronics module 670 may be electrically connected via backside tracers between the pads 634 and mounted to the substrate 636, for example. The electronics module 670 may comprise a tuning capacitor, for example, as will be described in more detail hereinafter.

Figure 13A:
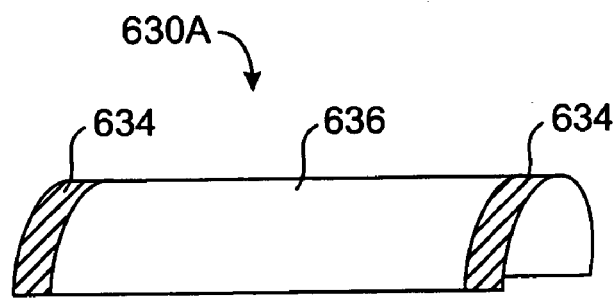
FIGS. 13A-13D illustrate alternative examples of electrode pad assemblies useful in the activation devices of the present invention.
Figure 13B:
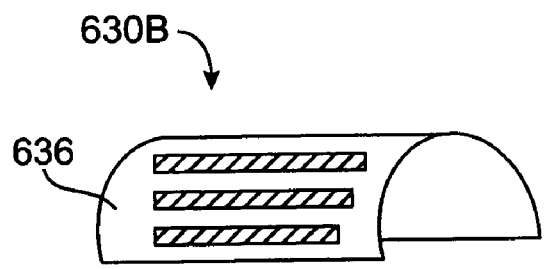
Figure 13C:
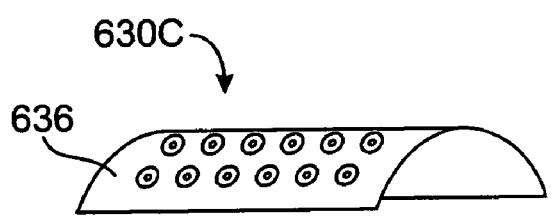
Figure 13D:
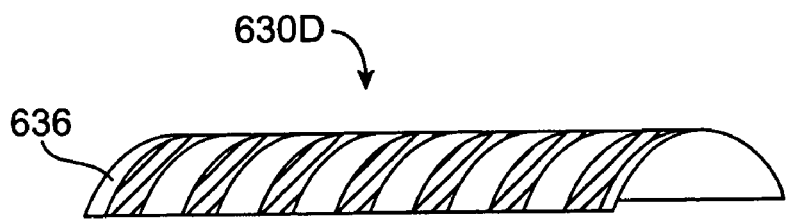

The assembly 630 may include both the receiving coil 632 and the electrode pads 634, or simply the electrode pads 634 without the coil 632 as when the device 620 is hard wired to the control system 60. In this latter instance, the electrode pads 634 may be shaped and arranged in a wide variety of manners, a few examples of which are shown in FIGS. 13A-13D. In FIG. 13A, the pads 634 are disposed about the ends of the substrate 636 substantially parallel to the circumference. In FIG. 13B, the pads are disposed about the mid portion of the substrate 636 substantially parallel to the longitudinal axis. In FIG. 13C, the electrode pads 634 comprise circles or concentric rings distributed about the substrate 636. In FIG. 13D, the pads 634 are disposed along the entire substrate 636 substantially parallel to the circumference.

Figure 14:
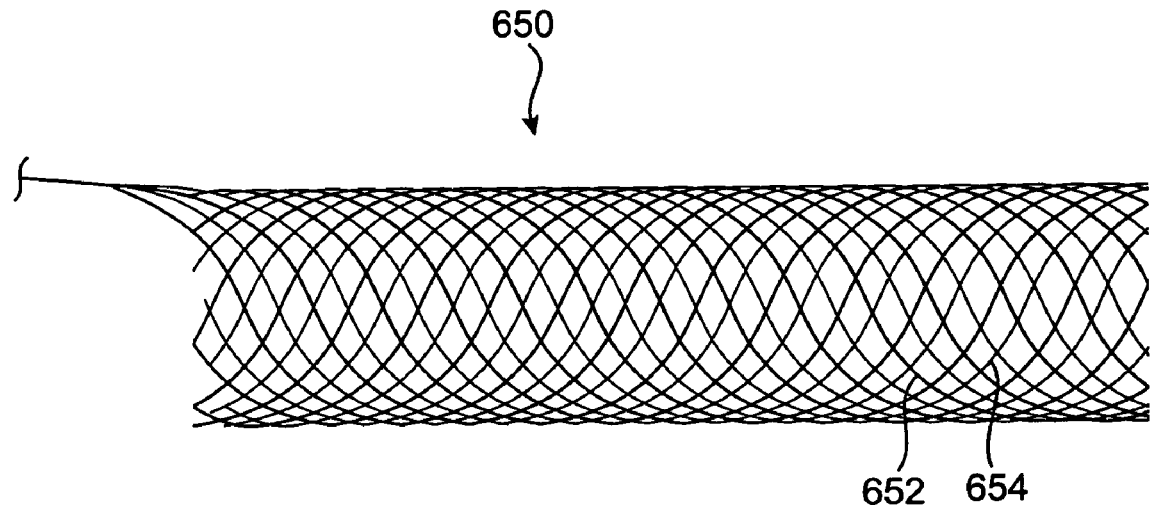
FIG. 14 illustrates an electrical intravascular baroreceptor activation device comprising a tubular braided stent-like structure.

Refer now to FIG. 14 which illustrates an electrical intravascular baroreceptor activation device 650 comprising a tubular braided stent like structure, for example. The intravascular electrical baroreceptor activation device 650 may comprise a wide variety of stent like structures including, without limitation, self expanding multi-filar braid, self expanding interconnected zig-zag bands, self expanding coil bands, etc. Generally speaking, for the intravascular stent like baroreceptor activation devices disclosed herein, elastic self expanding stent like structures may be preferred to avoid accidental collapse if the device is to be implanted in the carotid sinus which is relatively unprotected from external forces.

In addition, for electrical activation devices disclosed herein, it is generally desirable to limit unwanted collateral stimulation of adjacent tissues (i.e., to limit the electrical field beyond to vascular wall wherein the baroreceptors reside) by creating localized cells or electrical fields. Localized cells may be created, for example, by spacing the electrodes or poles very close together (e.g., <1 mm), placing the anode in a carotid artery and placing the cathode in an adjacent jugular vein (or vice versa), biasing the electrical filed with conductors and/or magnetic fields (e.g., an electrical field generator in the jugular vein with a conductive device in the carotid sinus to attract the e field), etc.

Alternatively, if it is desired to stimulate the carotid sinus nerve (CSN), the electrical field may be directed from one or more intravascular and/or extravascular electrical activation devices disposed near the CSN. For example, one electrode may be placed in the external carotid artery and another electrode may be placed in the internal carotid artery, or one electrode may be placed in the external carotid artery and another electrode may be placed in the jugular vein, etc. With this arrangement, the electrical field created between the electrodes may be used to stimulate the CSN for baropacing applications.

In the specific embodiment shown in FIG. 14, the braided tube structure 650 includes a plurality of interwoven members 652/654, one set 652 (e.g., half) of which are helically wound in one direction (e.g., CW) and another set 654 (e.g., the other half) of which are helically wound in the other direction (e.g., CCW). In FIG. 14, one set of members is shown in black thick lines and the other set is shown in gray thick lines (the thin lines represent members running along the back side of the tubular device 650). For example, in a 16 wire braid, 8 members run CW, and 8 members run CCW. One set of members 652 comprises electrically conductive wires, and the other set of members comprises electrically insulating members 654. The electrically conductive wires 652 may comprise a conductive metal such as MP 35N, SST, Elgiloy, or a NiTi alloy, and the electrically insulating members 654 may comprise a non-conductive material such as a polymer or a metal wire covered by a non-conductive insulating material, for example. Because the electrically conductive wires 652 run in the same helical direction, each wire remains electrically isolated from adjacent wires. In addition, the electrically insulating members 654 aid in maintaining the electrical isolation of each conductive wire 652 by maintaining the spacing between adjacent wires 652. To this end, each conductive wire 652 acts like a helically extending electrode.

Figure 15:
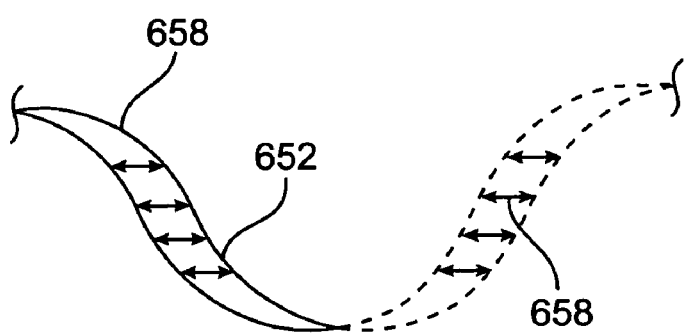
FIG. 15 is a detailed view of a portion of the stent structure of FIG. 14, showing a bipolar design.

Of the conductive members 652, adjacent members may have a dissimilar polarity so as to create current flow 658 between adjacent wires as shown in FIG. 15. For example, every other wire 652 may have a positive polarity, with every other remaining wire having a negative polarity (bipolar or anode/cathode arrangement). As such, the electrical field may be in the form of a series of helices having a width substantially equal to the spacing between adjacent wires 652. The wires 652 may have a bipolar, tripolar, or any other multipolar arrangement, depending on how each wire 652 is connected to and activated by the control system 60. The control system 60 (not shown) may be coupled to the conductive wires 652 by cable 656. Cable 656 may be hardwired to the control system 60 or wirelessly coupled to the control system by incorporating a receiver coil in or near the device 650. As with the prior embodiments, an electronics module 670 (not shown) may be electrically connected to adjacent wires 652.

Figure 16A:
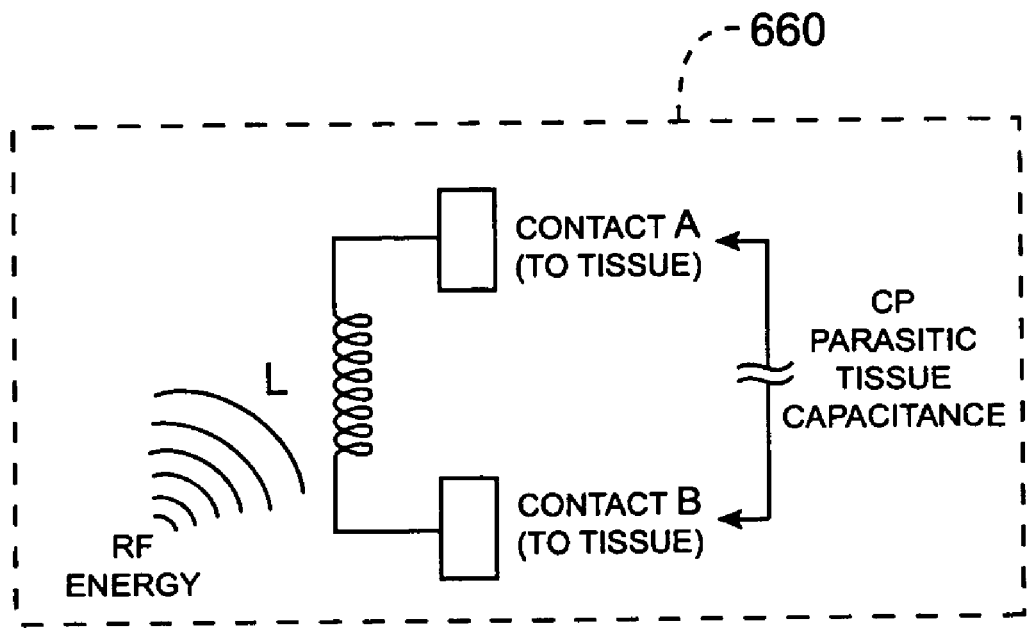
FIGS. 16A and 16B show electrical activation circuits useful in the apparatus of the present invention.
Figure 16B:
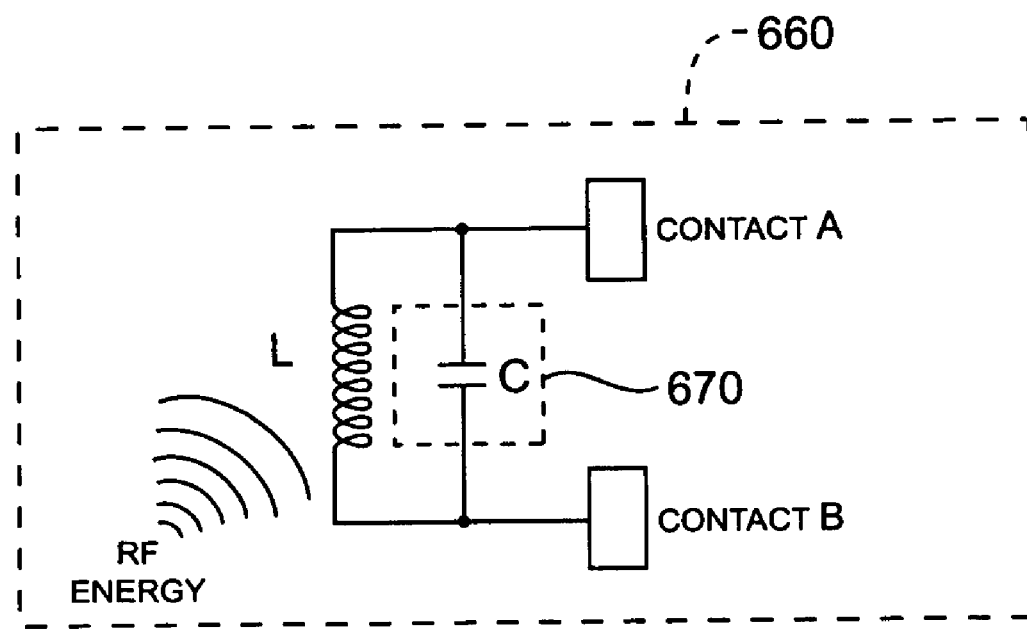

When implanted, the electrical activation embodiments may create an L C circuit as shown in the schematic 660 shown in FIG. 16A. In particular, an L C circuit may be created between electrode contacts when using a receiving coil (L) due to the parasitic capacitance (CP) of tissue (e.g., vascular wall tissue), and thus the device would potentially have a resonating frequency. Alternatively, an electronics module 670 such as a tuning circuit or a simple capacitor (C) may be employed to create an L C tuned circuit as shown in FIG. 16B. The EM or RF signal generated by the control system may be located within the body (e.g., neck) or outside the body.

Figure 17:
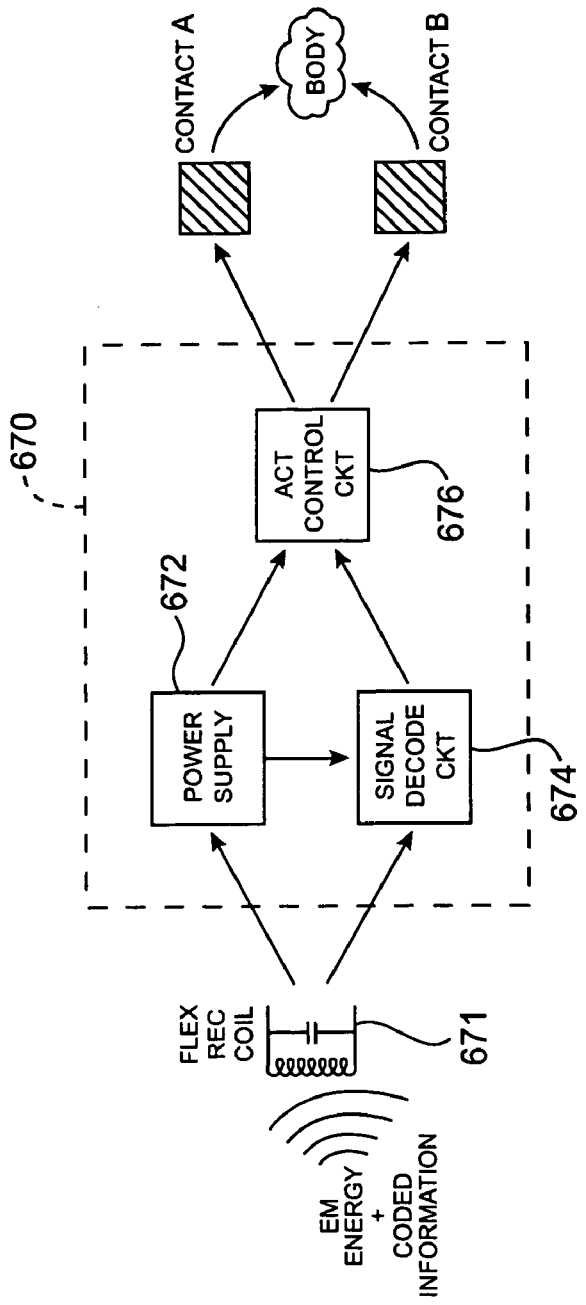
FIG. 17 shows an electrical baroreceptor activation device according to the present invention which incorporates an electronics module.
Figure 18:
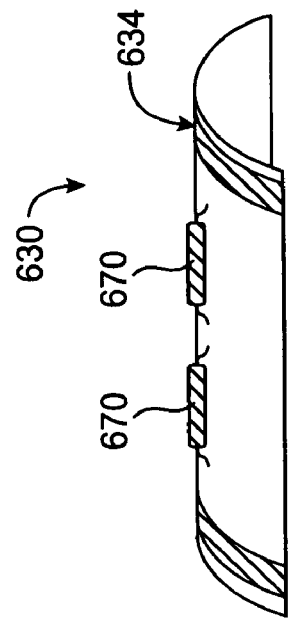
FIG. 18 shows the embodiment of FIG. 17 with the electronic module disposed on an electrode/receiver coil assembly.

The activation devices described herein may be passive with the intelligence carried by the control system 60. Alternatively, the activation devices may incorporate intelligence in the form of an electronics module 670 which cooperates with the control system 60 to actively control power transmission, activation energy, activation regimen, electrode activation sequencing, etc. For example, as seen in the schematic illustration of FIG. 17, (where reference to RF is intended to include all EM sources) the activation device may incorporate an electronics module 670. The electronics module 670 may be disposed on the electrode/receiver coil assembly 630 (to be deployed for example on a stent-like electrode assembly) as shown in FIG. 18. The electronics module 670 may include a power supply circuit 672 which receives power from the EM energy transmitted by the control system 60 to a receiver coil 671 of the activation device. The electronics module 670 may include a signal decoding circuit 674 to decode an encoded signal transmitted by the control system 60. The electronics module may also include an activation control circuit 676 that delivers the desired electrical signals to specific electrodes as a function of an internal algorithm and the decoded information received from circuit 674. Optionally, the module 670 may be configured to both receive and transmit back encoded information. Data to be sent backing include pressure, pulse, or other information obtained from sensors on the activation device or elsewhere.

Figure 19:
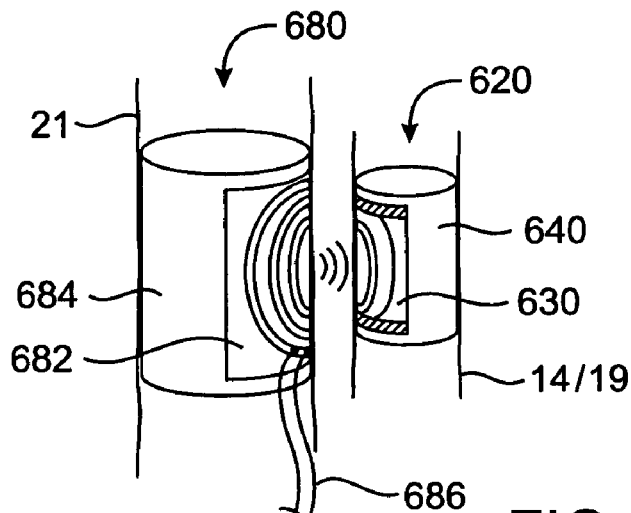
FIG. 19 is a schematic illustration of a wireless transmission arrangement where a coil activation device is implanted in an artery and a transmitting coil is implanted in an adjacent vein. The coils are aligned along a common axle.

Refer now to FIG. 19 which schematically illustrates a wireless transmission arrangement for use with any of the intravascular and extravascular electrical baroreceptor activation devices described herein. For sake of illustration and discussion only, intravascular electrical baroreceptor activation device 620 is shown in FIG. 19, including the flexible receiver coil and electrode circuit assembly 630 deployed on the outer surface of a stent-like or other electrode structure 640. The activation device 620 may be disposed in the artery containing the baroreceptors, such as internal carotid artery 19 or common carotid artery 14. A transmitting device 680 may be disposed in an adjacent vein such as jugular vein 21 which lies in close proximity to the internal carotid artery 19 and the common carotid artery 14.

In this embodiment, (FIG. 19) the transmitting device includes a coil assembly 682 disposed on a stent like tubular structure 684, similar to the construction and arrangement of assembly 630 disposed on stent like structure 640 as described previously. The coil assembly 682 emits an RF or other EM signal picked up by coil assembly 630 on the activation device 620. The coil assembly 682 on the transmitting device 680 acts as an antenna and is operably coupled to the control system 60 (not shown) via leads 686 which travel down the vein 21 to a remote entry site. The presence of leads 686 in the venous side of the vascular system is less concerning due to the reduced risk of thromboembolism and stroke.

FIG. 19 illustrates coupling between two generally "planar" coils which are arranged face-to-face in adjacent blood vessels. FIGS. 19A-19C illustrate alternative embodiments. In FIG. 19A, a helical transmitting coil 691 is positioned in a first blood vessel and a helical receiving coil 693 is positioned in a second blood vessel immediately adjacent the transmitting coil. The coil axes are aligned, and transmissions may be made as described previously. The coils 691 and 693 may also be arranged with parallel axes, but longitudinally separated, as shown in FIG. 19B, and a specific implantation in the common carotid artery CC is shown if FIG. 19C.

Figure 20:
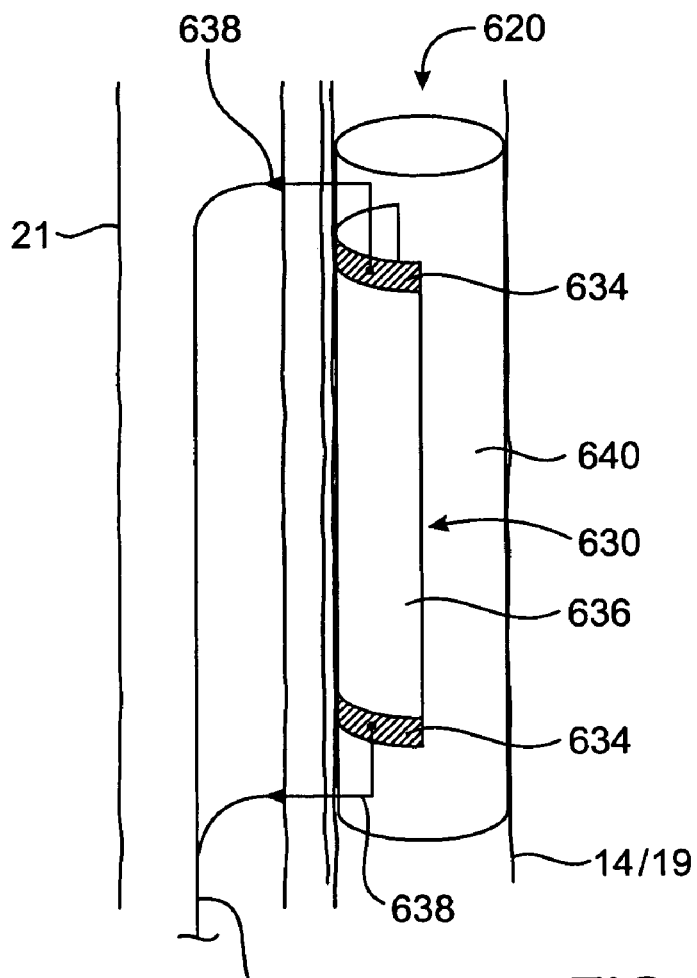
FIG. 20 shows an implanted baroreceptor activation device which hard wired to a control system in the lumen of an adjacent vein.

As an alternative to wireless transmission, the activation device 620 may be hard wired to the control system 60 as shown in FIG. 20. In this embodiment, the activation device 620 may be disposed in the artery containing the baroreceptors, such as internal carotid artery 19 or common carotid artery 14. The activation device includes two or more laterally facing extensions or barbs 638 which extend through the arterial wall and into an adjacent vein such as jugular vein 21, which lies in close proximity to the internal carotid artery 19 and the common carotid artery 14. The electrode pads 634 are electrically connected to the extensions 638 which are coupled to the control system 60 (not shown) via leads 639 which travel down the vein 21 to a remote entry site. The presence of leads 639 in the venous side of the vascular system is less concerning due to the reduced risk of thromboembolism and stroke.

Refer now to FIGS. 21-25 which schematically illustrate tools and methods for making a connection between an electrical activation device disposed in or on a vessel containing baroreceptors (e.g., carotid artery 14/19) and leads disposed in an adjacent vessel (e.g., jugular vein 21). The tools and methods described with reference to FIGS. 21-25 facilitate minimally invasive transluminal techniques, and presume the activation device 650 has been previously implanted by minimally invasive transluminal techniques, for example. These tools and methods may be applied to many of the intravascular electrical activation devices described herein, and are described with reference to braided stent like structure 650 for sake of illustration, not limitation.

Figure 21:
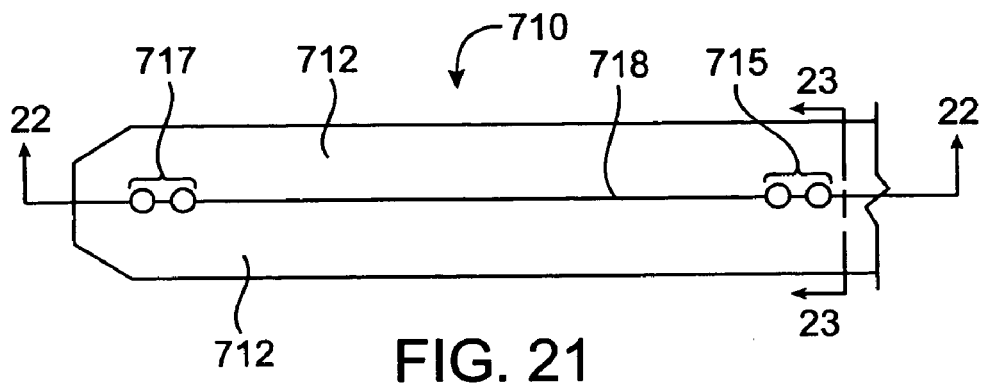
FIGS. 21-24 illustrate a catheter system including a stylet which may be used to implant and electrically connect a baroreceptor activation device in accordance with the principles of the present invention.
Figure 22:
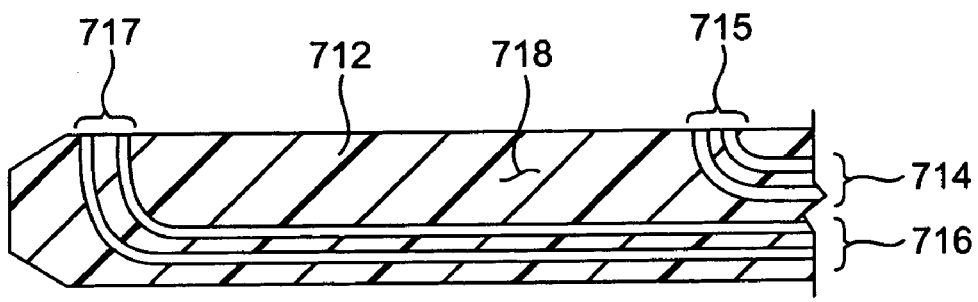
Figure 23:
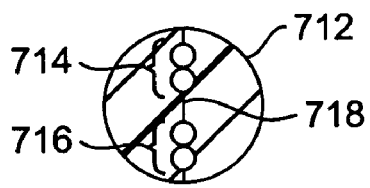
Figure 24:
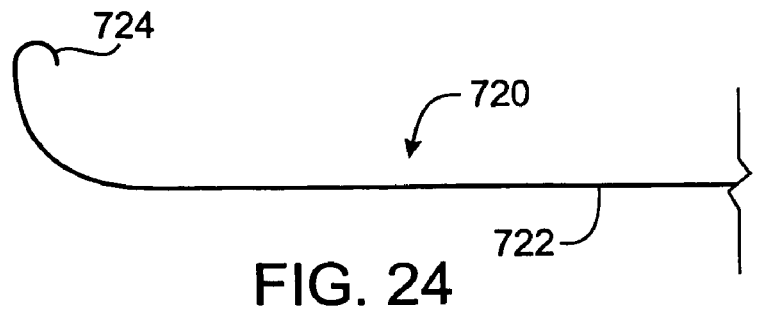

FIG. 24 illustrates a top view of a distal portion of a delivery catheter 710. Catheter 710 is sized and adapted for intravascular insertion and navigation from a remove vascular access point leading to the jugular vein 21 adjacent the carotid sinus 20. FIG. 22 is a longitudinal sectional view taken along line 22-22 in FIG. 21, and FIG. 23 is a cross sectional view taken along line 23-23 in FIG. 21. As may be seen in FIGS. 21-23, catheter 710 includes an elongate shaft 712 with a first pair of lumens 714 leading to proximal ports 715, and a second pair of lumens 716 leading to distal ports 717. A plane of separability 718 such as a peelable scam may be provided along the centerline of the shaft 712 to permit subsequent removal over the leads as will be described in more detail hereinafter.

FIG. 25 illustrates a distal portion of a curved stylet 720 formed of a flexible metal such as NiTi, for example. The stylet 720 includes an elongate shaft 722 that is sized and adapted to be inserted and advanced through the lumens 714/716 of the delivery catheter 710. The distal end of the stylet 720 includes a sharpened tip 724 to facilitate tissue penetration. A distal portion of the stylet 720 includes a primary curve 726 having a resting nominal diameter roughly equal to the distance between the center points of the ports 715/717 of the delivery catheter 710. The distal portion of the stylet 720 may also include a secondary curve 728 to facilitate orientation of the primary curve 726 relative to the catheter 710 as the stylet is advanced out of the ports 715/717.

Figure 25A:
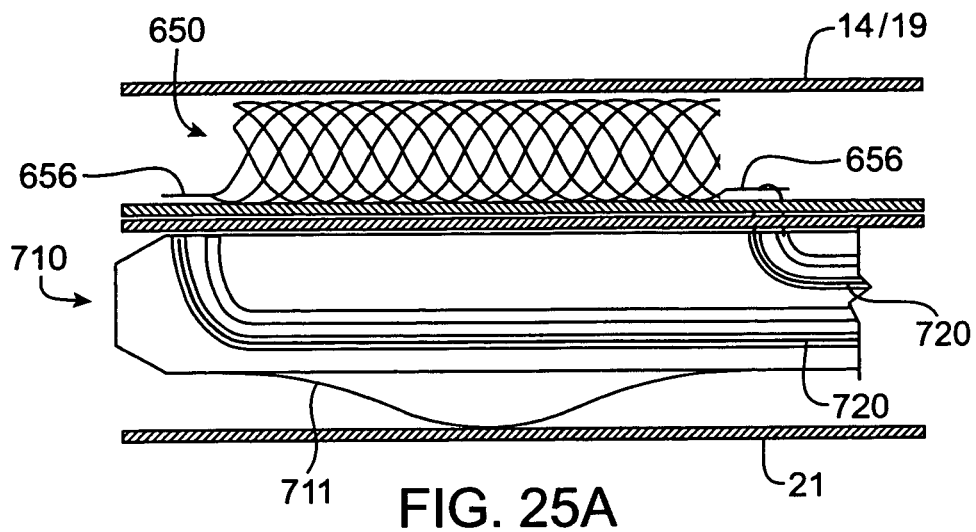
FIGS. 25A-25C illustrate a method of using the delivery catheter of FIGS. 21-24 for electrically connecting a braided stent-like activation structure in accordance with the principles of the present invention.
Figure 25B:
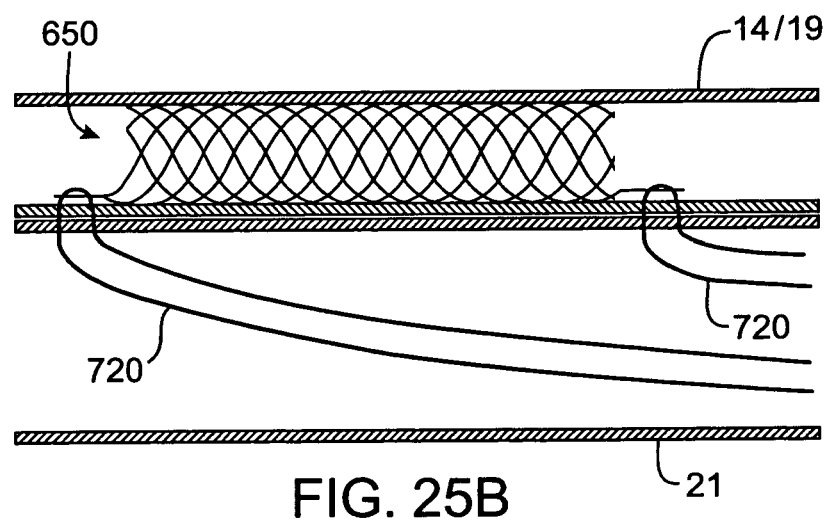
Figure 25C:
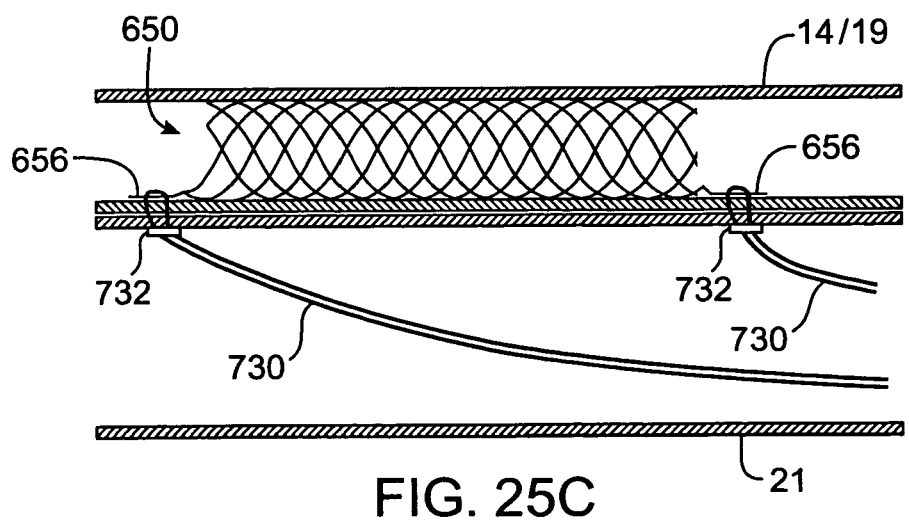

Refer now to FIGS. 25A-25C which illustrate a method of using the delivery catheter 710 and two stylets 720 to make an electrical connection to the braided stent like structure 650. To facilitate connection to the two different sets of conductive members 652 as described previously, two separate and relatively short tail leads 656 are provided corresponding to each set of conductive members 652. The short tail leads 656 may be uninsulated to ensure good electrical connection. Optionally, a biasing member 711 such as a deflection wire or eccentric balloon may be incorporated into the delivery catheter 710 to urge the ports 715/717 into contact with the inside surface of the vein 19.

The delivery catheter 710 is navigated to the jugular vein 21 until the distal portion thereof is adjacent the activation device 650 previously deployed in the artery 14/19 as seen in FIG. 25A. Stylets 720 are then advanced through one lumen in each pair of lumens 714/716 until the distal ends of the stylets 720 exit the ports 715/717. The distal ends 724 exit the ports 715/717, penetrate through the wall of the vein 21, penetrate through the wall of the artery 14/19, and wrap around the tail leads 656 due to the curved portion 726. Further advancement of the stylets 720 cause the tips 724 to reenter the ports 715/717 as shown with the proximal stylet 720 shown in FIG. 25A. The stylets 720 may be fully advanced along a return path through another of the pair of lumens 714/716 until the proximal and distal ends of the stylets 720 extend out the proximal end of the delivery catheter 710, after which the catheter 710 may be removed from the stylets 720 along the plane of separability 718 as seen in FIG. 25B.

Flexible leads 730 are then attached to the stylets 720 by connection one end of each lead 730 to one end of each stylet 720, respectively. The other ends of the stylets 720 may then be pulled proximally to thread the leads through the lumen of the vein 21 and around the lead tails 656 as shown in FIG. 25C. The lead wires 730 may comprise a conductive metal such as MP35N twisted cable or braid. After the leads 730 are in place, friction clamps 732 may be advanced thereover with a push catheter (not shown) to snug the leads 730 around the lead tails 656. Insulating tubular jackets (not shown) may then be placed over the lead wires 730, and the leads 730 may then be attached to the control system 60 and operated as described elsewhere herein.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method for activating a baroreflex, said method comprising:

transmitting a control signal from a transmitting coil implanted in a vein proximate the baroreceptor;

wherein the control signal is wirelessly received by an activation device comprising both (a) an electrode structure and (b) a receiving coil, separately formed from the electrode structure wherein the activation device is implanted in or on a blood vessel proximate to the baroreceptor, whereby the control signal induces electrical current in the receiving coil, which current flows to the electrode structure which activates the baroreceptor to produce a baroreflex.

2. A method as in claim 1, wherein the control signal is transmitted from a location in the vein adjacent to the baroreceptor.

3. A method as in claim 2, wherein the control signal is generated by a control system implanted remotely from an arterial baroreceptor, wherein the control system is wired through a venous lumen to a transmitter in the vein adjacent to the arterial baroreceptor.

* * * * *

UNITED STATES PATENT AND TRADEMARK OFFICE
CERTIFICATE OF CORRECTION

PATENT NO. : 7,616,997 B2
APPLICATION NO. : 10/402393
DATED : November 10, 2009
INVENTOR(S) : Kieval et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 959 days.

Signed and Sealed this

Nineteenth Day of October, 2010

David J. Kappos
*Director of the United States Patent and Trademark Office*